United States Patent
Kirschenman et al.

(10) Patent No.: US 8,641,663 B2
(45) Date of Patent: Feb. 4, 2014

(54) ROBOTIC CATHETER SYSTEM INPUT DEVICE

(75) Inventors: Mark B. Kirschenman, Waverly, MN (US); John A. Hauck, Shoreview, MN (US); Jane J. Song, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 12/933,063

(22) PCT Filed: Mar. 27, 2009

(86) PCT No.: PCT/US2009/038618
§ 371 (c)(1),
(2), (4) Date: Sep. 16, 2010

(87) PCT Pub. No.: WO2009/120992
PCT Pub. Date: Oct. 1, 2009

(65) Prior Publication Data
US 2011/0015569 A1   Jan. 20, 2011

Related U.S. Application Data

(60) Provisional application No. 61/141,971, filed on Dec. 31, 2008, provisional application No. 61/099,904, filed on Sep. 24, 2008, provisional application No. 61/040,143, filed on Mar. 27, 2008, provisional application No. 61/040,142, filed on Mar. 27, 2008, provisional application No. 61/040,141, filed on Mar. 27, 2008.

(51) Int. Cl.
*A61M 31/00* (2006.01)
*A61M 37/00* (2006.01)
*A61M 5/20* (2006.01)

(52) U.S. Cl.
USPC ............... 604/95.01; 604/96.01; 604/156

(58) Field of Classification Search
USPC ............. 604/66–67, 95.01, 95.02, 95.04, 604/131–133, 154, 156
See application file for complete search history.

(56) References Cited

U.S. PATENT DOCUMENTS

| | | | |
|---|---|---|---|
| 3,605,725 | A | 9/1971 | Bentov |
| 4,802,487 | A | 2/1989 | Martin et al. |

(Continued)

FOREIGN PATENT DOCUMENTS

| | | |
|---|---|---|
| GB | 2397177 | 7/2007 |
| JP | H10216238 | 8/1998 |

(Continued)

OTHER PUBLICATIONS

"International Search Report & Written Opinion", PCT/US2009/069712 Feb. 25, 2010.

*Primary Examiner* — Manuel Mendez
*Assistant Examiner* — Rebecca E Eisenberg
(74) *Attorney, Agent, or Firm* — Dykema Gossett PLLC

(57) ABSTRACT

An input device for a robotic medical system includes a handle configured to be rotatable about a center axis, and to be longitudinally displaceable along the center axis. The input device also includes a deflection control element disposed on the handle and configured to selectively control deflection of the distal end of a flexible medical instrument electrically coupled to the input device. Longitudinal displacement of the handle may cause or result in a corresponding longitudinal motion or deflection of the flexible medical instrument. Rotation of the handle may cause or result in a corresponding rotation of the deflection plane. Longitudinal displacement and rotation of the handle may be detected or sensed electronically.

24 Claims, 25 Drawing Sheets

(56) References Cited

U.S. PATENT DOCUMENTS

| | | | |
|---|---|---|---|
| 4,884,557 | A | 12/1989 | Takehana et al. |
| 4,962,448 | A | 10/1990 | DeMaio et al. |
| 5,107,080 | A | 4/1992 | Rosen et al. |
| 5,170,817 | A | 12/1992 | Sunderland et al. |
| 5,318,525 | A | 6/1994 | West et al. |
| 5,441,483 | A | 8/1995 | Avitall |
| 5,449,345 | A | 9/1995 | Taylor et al. |
| 5,545,200 | A | 8/1996 | West et al. |
| 5,579,442 | A | 11/1996 | Kimoto et al. |
| 5,607,462 | A | 3/1997 | Imran |
| 5,630,783 | A | 5/1997 | Steinberg |
| 5,706,827 | A | 1/1998 | Ehr et al. |
| 5,784,542 | A | 7/1998 | Ohm et al. |
| 5,791,908 | A | 8/1998 | Gillio |
| 5,800,178 | A | 9/1998 | Gillio |
| 5,807,377 | A | 9/1998 | Madhani et al. |
| 5,808,665 | A | 9/1998 | Green |
| 5,828,813 | A | 10/1998 | Ohm |
| 5,854,622 | A | 12/1998 | Brannon |
| 6,040,758 | A | 3/2000 | Sedor et al. |
| 6,063,095 | A * | 5/2000 | Wang et al. .................. 606/139 |
| 6,113,395 | A | 9/2000 | Hon |
| 6,290,683 | B1 | 9/2001 | Erez et al. |
| 6,348,911 | B1 | 2/2002 | Rosenberg et al. |
| 6,396,232 | B2 | 5/2002 | Haanpaa et al. |
| 6,432,112 | B2 | 8/2002 | Brock et al. |
| 6,500,167 | B1 | 12/2002 | Webster |
| 6,709,667 | B1 | 3/2004 | Lowe et al. |
| 6,850,252 | B1 | 2/2005 | Hoffberg |
| 6,869,390 | B2 | 3/2005 | Elliott et al. |
| 6,869,396 | B2 | 3/2005 | Belson |
| 7,199,790 | B2 | 4/2007 | Rosenberg et al. |
| 7,263,397 | B2 | 8/2007 | Hauck et al. |
| 7,276,044 | B2 | 10/2007 | Ferry et al. |
| 7,698,966 | B2 | 4/2010 | Gosselin |
| 7,850,642 | B2 | 12/2010 | Moll et al. |
| 8,317,744 | B2 | 11/2012 | Kirschenman |
| 8,317,745 | B2 | 11/2012 | Kirschenman et al. |
| 8,390,438 | B2 | 3/2013 | Olson et al. |
| 2001/0018591 | A1 | 8/2001 | Brock et al. |
| 2002/0068868 | A1 | 6/2002 | Thompson et al. |
| 2002/0072704 | A1 | 6/2002 | Mansouri-Ruiz |
| 2002/0087048 | A1 | 7/2002 | Brock et al. |
| 2003/0018232 | A1 | 1/2003 | Elliott |
| 2004/0193239 | A1 | 9/2004 | Falwell et al. |
| 2005/0075538 | A1 | 4/2005 | Banik et al. |
| 2005/0203382 | A1 | 9/2005 | Govari et al. |
| 2005/0222554 | A1 | 10/2005 | Wallace et al. |
| 2006/0052664 | A1 | 3/2006 | Julian et al. |
| 2006/0089637 | A1 | 4/2006 | Werneth et al. |
| 2006/0137476 | A1 | 6/2006 | Bull et al. |
| 2006/0155321 | A1 | 7/2006 | Bressler et al. |
| 2006/0276775 | A1 | 12/2006 | Rosenberg et al. |
| 2006/0293643 | A1 | 12/2006 | Wallace et al. |
| 2007/0043338 | A1 | 2/2007 | Moll et al. |
| 2007/0135803 | A1 | 6/2007 | Belson |
| 2007/0142726 | A1 | 6/2007 | Carney et al. |
| 2007/0185486 | A1 | 8/2007 | Hauck et al. |
| 2007/0197896 | A1 | 8/2007 | Moll et al. |
| 2007/0197939 | A1 | 8/2007 | Wallace et al. |
| 2007/0198008 | A1 | 8/2007 | Hauck et al. |
| 2007/0233044 | A1 | 10/2007 | Wallace |
| 2007/0233045 | A1 | 10/2007 | Weitzner et al. |
| 2007/0270685 | A1 | 11/2007 | Kang et al. |
| 2007/0298877 | A1 | 12/2007 | Rosenberg et al. |
| 2008/0009791 | A1 | 1/2008 | Cohen et al. |
| 2008/0013809 | A1 | 1/2008 | Zhu et al. |
| 2008/0312536 | A1 | 12/2008 | Dala-Krishna |
| 2009/0033623 | A1 | 2/2009 | Lin |
| 2009/0247993 | A1 | 10/2009 | Kirschenman et al. |
| 2009/0322697 | A1 | 12/2009 | Cao |
| 2012/0277663 | A1 | 11/2012 | Millman et al. |
| 2013/0006268 | A1 | 1/2013 | Swarup et al. |

FOREIGN PATENT DOCUMENTS

| | | |
|---|---|---|
| JP | 2003024336 | 1/2003 |
| WO | WO-96/39944 | 12/1996 |
| WO | WO-2006/120666 | 11/2006 |
| WO | WO-2007/098494 | 8/2007 |
| WO | WO-2007088208 | 8/2007 |
| WO | WO-2007/120329 | 10/2007 |
| WO | WO-2007/136803 | 11/2007 |
| WO | WO-2007146325 | 12/2007 |
| WO | WO-2008/101228 | 8/2008 |
| WO | WO-2009/120982 | 10/2009 |
| WO | WO-2009/120992 | 10/2009 |

* cited by examiner

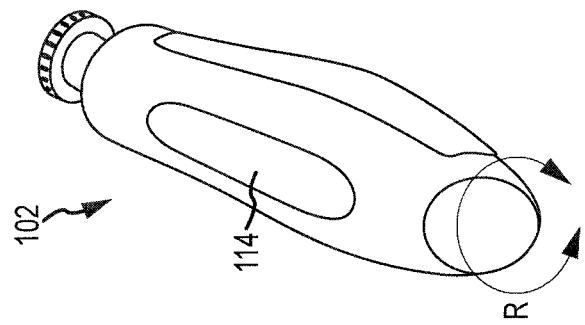
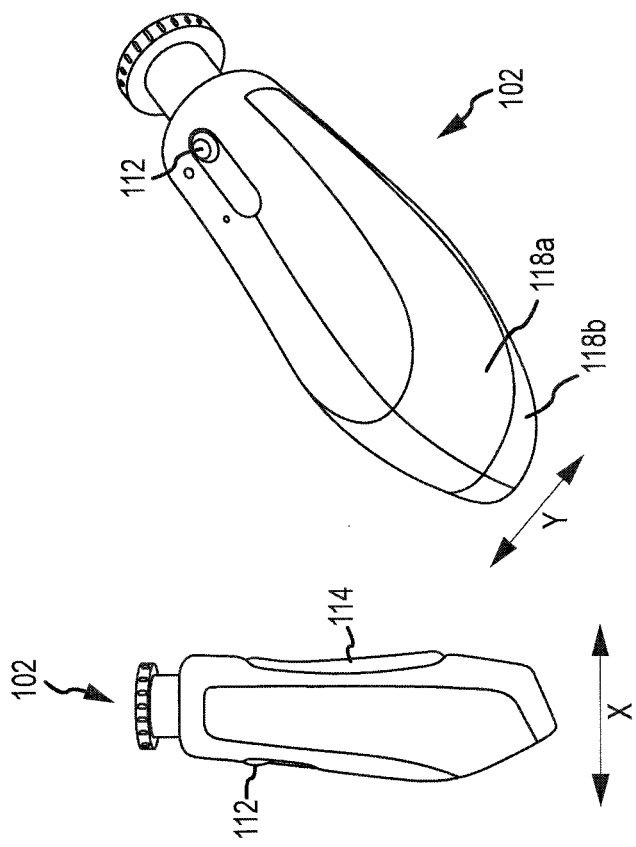

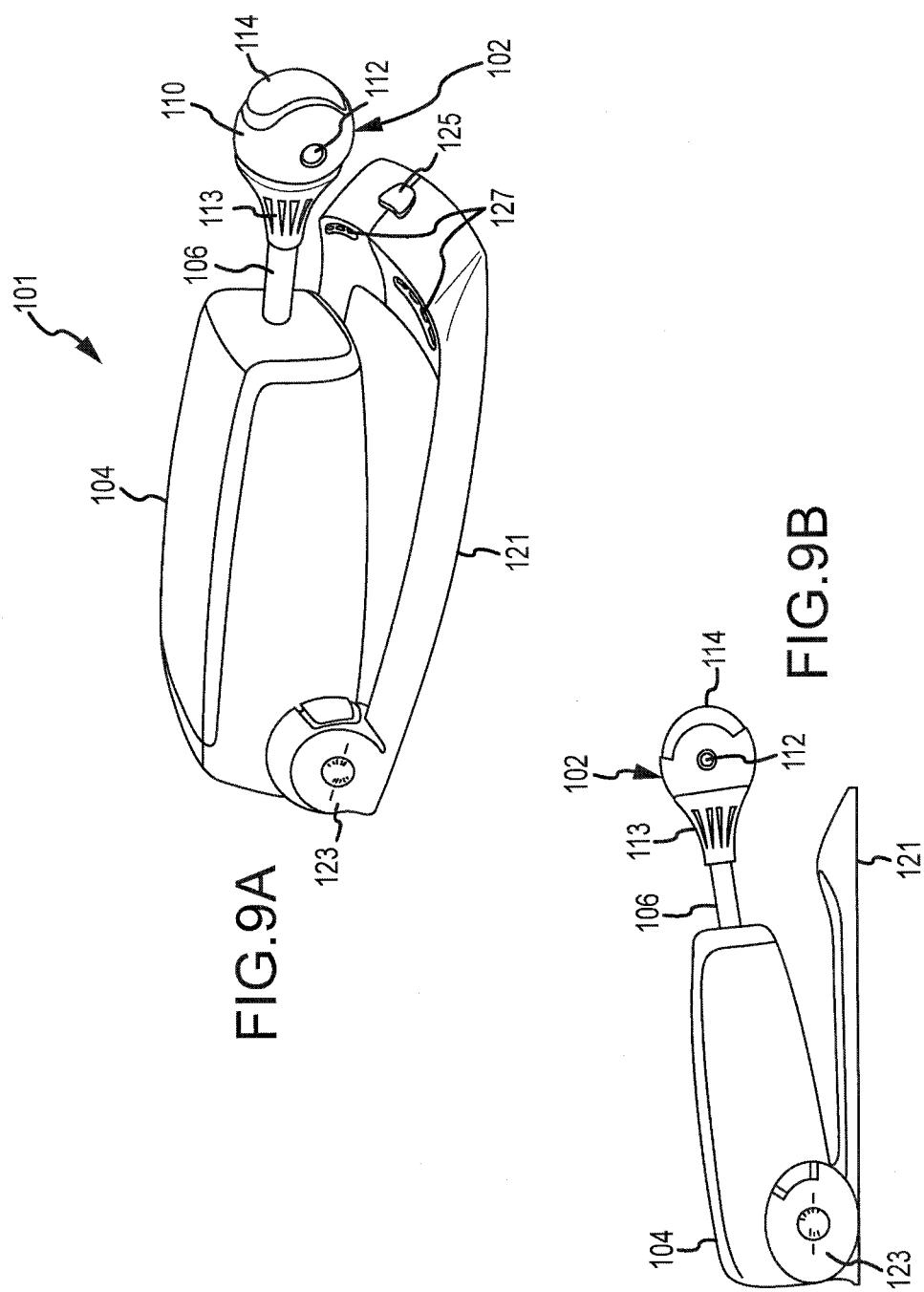

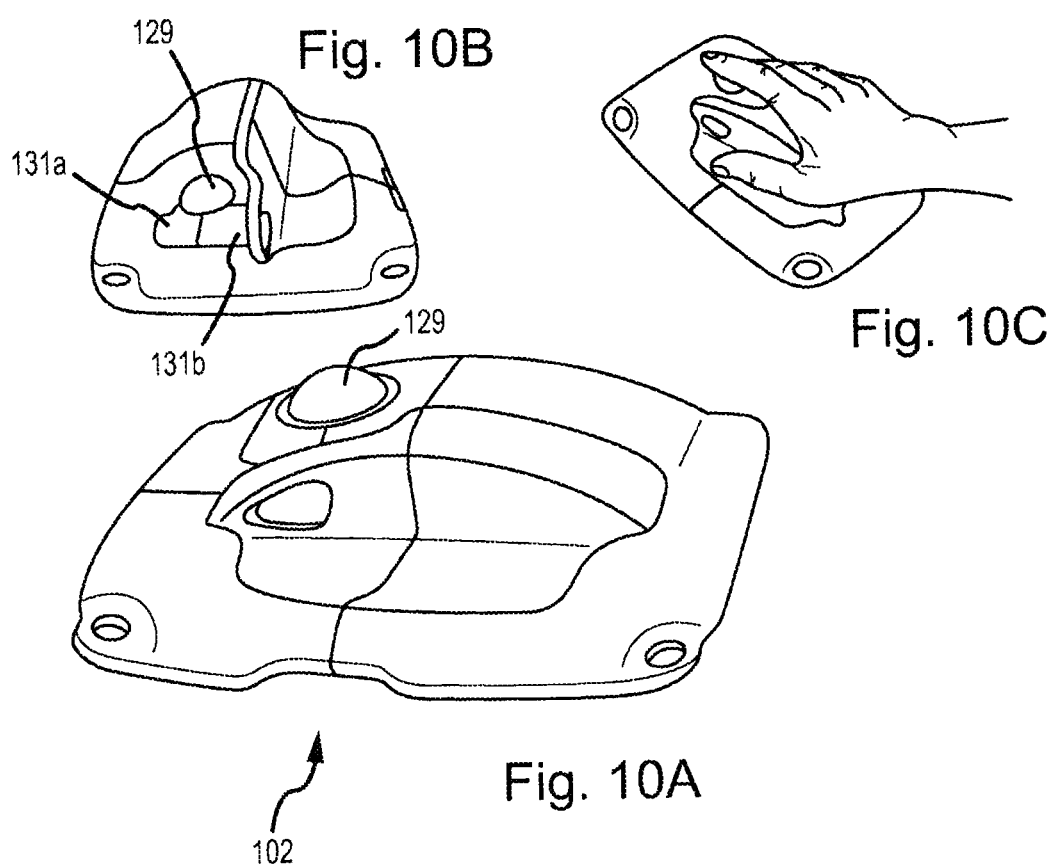

ROBOTIC CATHETER SYSTEM INPUT DEVICE

CROSS-REFERENCE TO RELATED APPLICATIONS

This application claims the benefit of priority to U.S. provisional application Nos. 61/040,141, filed Mar. 27, 2008; 61/040,142, filed Mar. 27, 2008; 61/040,143, filed Mar. 27 2008; 61/099,904, filed Sep. 24, 2008; and 61/141,971, filed Dec. 31, 2008, the entire disclosures of which are hereby incorporated by reference as though fully set forth herein.

BACKGROUND OF THE INVENTION a. Field of the Invention

The present invention relates to robotic catheter systems, and more particularly, to improved input devices for controlling movement of catheters and sheaths within a treatment area, such as a cardiac chamber. Input devices according to the present teachings may also be used with other computer-based medical systems, such as simulation systems for training.

b. Background Art

Electrophysiology catheters are used for an ever-increasing number of procedures. For example, catheters have been used for diagnostic, therapeutic, mapping and ablative procedures, to name just a few examples. Typically, a catheter is manipulated through the patient's vasculature to an intended site, for example, a site within the patient's heart, and carries one or more electrodes, which may be used for mapping, ablation, diagnosis, or other treatments.

Traditional techniques of manipulating catheters to, and within, a treatment area typically include a physician manipulating a handle connected to a catheter. The handle generally includes a mechanism directly connected to guide wires for controlling the deflection of a catheter. A second handle is generally provided for controlling deflection of a sheath. Rotating and advancing a catheter or sheath generally requires an electrophysiologist (EP) to physically rotate and advance the associated handle.

Recently, catheter systems have been developed that work in concert with visualization/mapping systems, such as the NavX™ or EnSite™ systems commercialized by St. Jude Medical, Inc. However, conventional systems still generally involve an EP manually controlling a catheter and sheath system, and associated visualization systems typically reactively monitor catheter movement.

BRIEF SUMMARY OF THE INVENTION

Systems are provided for receiving user inputs and providing signals representative of the user inputs to a catheter system, which may be a robotic catheter system. An embodiment of a robotic catheter system (also referred to as "the system") may be used, for example, to manipulate the location and orientation of sheaths and catheters in a heart chamber or in another body portion. The system may incorporate a human input device, e.g., a joystick, configured for interaction with a user; an electronic control system that translates motion of the user at the input device into a resulting movement of a catheter tip; and a visualization device that provides a user with real-time or near-real-time positioning information concerning the catheter tip. The system may provide the user with a similar type of control provided by a conventional manual system, and allow for repeatable, precise, and dynamic movements. The input system may thus provide a user, such as an electrophysiologist, with an input device that mimics a device the user already understands and is familiar with.

In an embodiment, the input device includes a first handle and a second handle. The first handle and the second handle may be aligned coaxially along a shaft. The handles may include selector switches, dials or buttons such as, for example, slider switches or thumb wheels, which may be configured to control movement of the catheter and the sheath. Handles may be longitudinally displaceable along a shaft, and may be configured such that longitudinal displacement of a shaft results in a longitudinal displacement of the associated catheter/sheath. In an embodiment, the input device may include a single handle configured to control the sheath and catheter, either together or independently. In embodiments, the input device may include a selector mechanism, such as a three position switch, through which a user may selectively control the catheter, the sheath, or both the catheter and sheath.

In an embodiment, an input device may include one or more indicators configured to provide an indication to a user concerning whether a catheter, a sheath, or both a catheter and a sheath, are selected for control. For example, input devices may include an LED indicator (e.g., a white LED) to indicate a catheter is selected for control, and another LED (e.g., a blue LED) to indicate a sheath is selected for control.

In an embodiment, an input device may include a device control switch that must be activated before the user input will transmit signals indicative of user inputs. For example, a system in communication with an input device may be configured to accept inputs from user input device only when a device control switch is activated.

A system according to the present teachings may be configured to receive the inputs from the user input control, and to transmit the user inputs to a robotic catheter system configured to cause corresponding motion of a catheter system.

BRIEF DESCRIPTION OF THE DRAWINGS

FIGS. 7G-7I are side and isometric views of still another embodiment of a handle for an input device.

FIGS. 9A and 9B are views of an input device according to an embodiment, FIG. 9A being an isometric view and FIG. 9B being a side elevation view.

FIGS. 10A, 10B, and 10C are isometric views of an input device according to an embodiment.

DETAILED DESCRIPTION OF THE INVENTION

Figure 1:
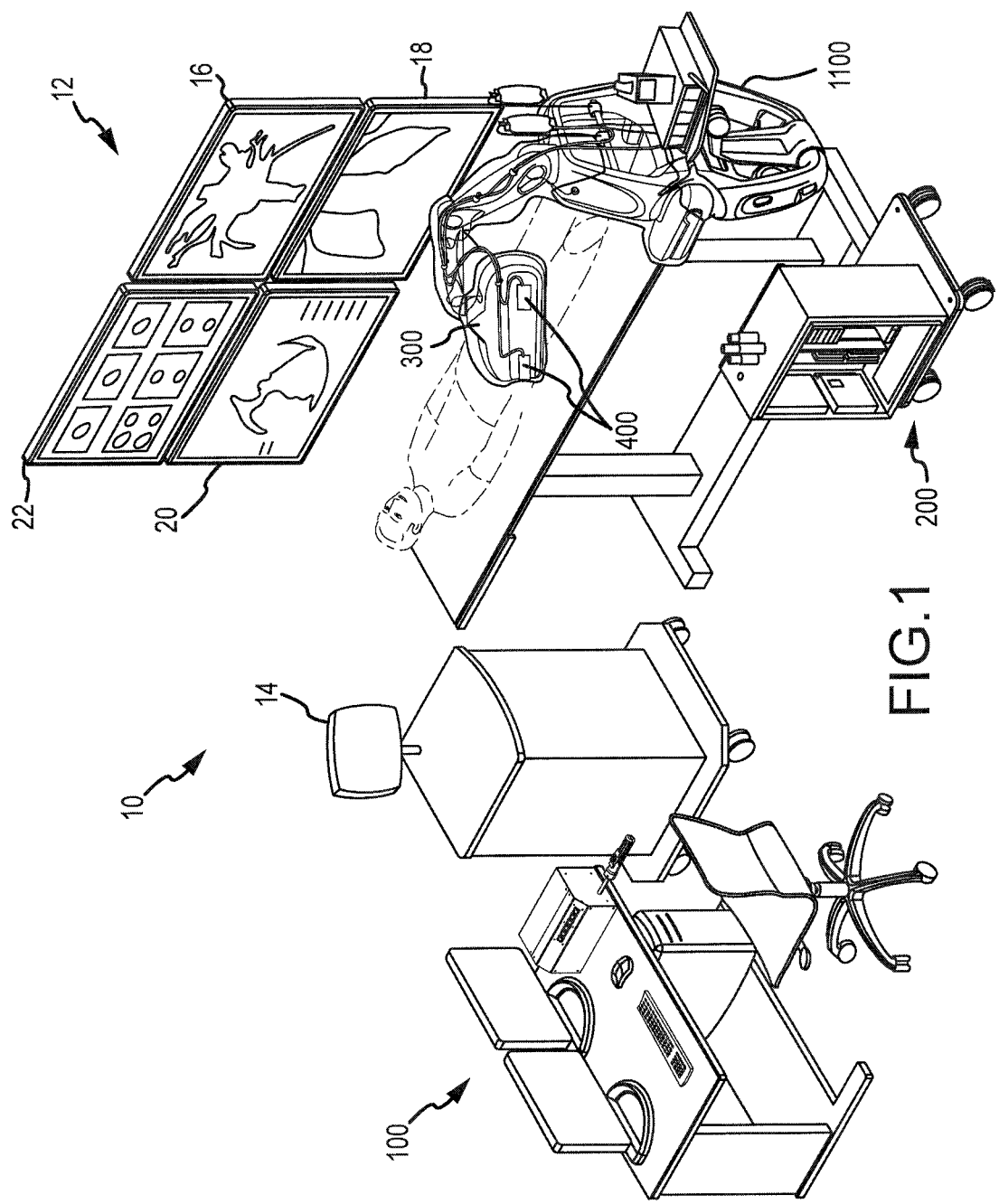
FIG. 1 is an isometric representation of a robotic catheter system according to an embodiment.

Referring now to the drawings wherein like reference numerals are used to identify like components in the various views, an embodiment of a robotic catheter system 10 (described in detail in co-pending application titled "Robotic Catheter System" filed Sep. 24, 2008, hereby incorporated herein by reference in its entirety), also referred to as "the system," is illustrated. The system 10 may be used, for example, to manipulate the location and orientation of catheters and sheaths in a treatment area, such as within a heart chamber or another body cavity. As generally illustrated in FIG. 1, system 10 may include an input control system 100. Input control system 100 may include an input device, such as a joystick, and related controls (further described below), that a user such as an electrophysiologist (EP) may interact with. Input control system 100 may be coupled to an electronic control system 200 that translates motions of the user at or with respect to the input device into a resulting movement of a catheter tip. A visualization system 12 may provide a user with real-time or near-real-time positioning information concerning the catheter tip. The system 10 may further include a closed-loop feedback system 14, for example, an EnSite NavX™ system, a magnetic positioning system, and/or optical force transducers. The system 10 may additionally include a robotic catheter manipulator assembly 300 for operating a robotic catheter device cartridge 400, and manipulator support structure 1100. The system 10 provides the user with a similar type of control provided by a conventional manual system, but allows for repeatable, precise, and dynamic movements. In an embodiment, certain elements described above with respect to system 10 may be omitted, or may be combined. For example, while electronic control system 200 is illustrated as a stand-alone unit, it is understood that it may be incorporated into another device, such as manipulator support structure 1100.

Input control system 100 may permit a user to control the movement and advancement of both a catheter and sheath. Generally, several types of input devices may be employed. The subject input devices of this teaching include, without limitation, instrumented catheter handle controls which may comprise one or more joysticks generally resembling traditional catheter controls. In embodiments, for example and without limitation, the input device may be self-centering, so that a movement from the center position causes an incremental movement of the actual catheter tip. Alternatively, the input device may work in absolute terms. Haptic feedback may also be employed in connection with the input device or input control system 100 to provide a user with a physical indication associated with contact (e.g., an indication when contact has been made). By way of example, and without limitation, haptic feedback may include heating or cooling a handle of the input device (e.g., to provide a user with an indication as to electrode temperature); vibrating a handle (e.g., to indicate contact with tissue); and/or providing resistance to movement of the input device. In addition to being indicative of contact, haptic feedback may also be employed to represent physical limitations of a device. For example, haptic feedback may be provided to indicate that a catheter or sheath has reached the end of available translation, achieved a maximum deflection, and/or to indicate another physical property of an associated medical device. In an embodiment, vibrating a handle, or providing resistance to movement, may be implemented using one or more motors coupled or in operative communication with a handle.

Many additional features may be included with the system 10, which may be used to help improve the accuracy and/or effectiveness of the system. Such features may include providing feedback using a visualization system 12, employing a magnetic positioning system, (e.g., for creating cardiac chamber geometries or models), displaying activation timing and voltage data, etc. Such features may be useful to, e.g., identify arrhythmias, guide precise movement of catheters or optical force transducers, etc. Additional features may include active tensioning of "passive" steering wires to reduce the system response time; cumulative ablation while an electrode tip is following a front-to-back ironing motion; and/or reactive/resistive impedance monitoring.

System 10 may include visualization system 12 which may provide a user with real-time or near-real-time positioning information concerning the catheter tip. In an exemplary embodiment, system 12 may include a monitor 16 for displaying cardiac chamber geometries or models, displaying activation timing and voltage data to identify arrhythmias, and for facilitating guidance of catheter movement. A fluoroscopy monitor 18 may be provided for displaying a real-time x-ray image for assisting a physician with catheter movement. Additional exemplary displays may include an Intracardiac Echo ("ICE") and EP Pruka displays, 20, 22, respectively.

Referring further to FIG. 1, aspects of system 14 will be additionally described.

System 14 (which may be of the type described in detail in U.S. Pat. No. 7,263,397, titled "Method and Apparatus for Catheter Navigation and Location and Mapping in the Heart,") may be provided for creating realistic cardiac chamber geometries or models, displaying activation timing and voltage data to identify arrhythmias, and guiding precise catheter movement. System 14 may collect electrical data from catheters, may use this information to track or navigate catheter movement, and may construct three-dimensional (3-D) models of the chamber.

As generally shown in FIG. 1, robotic catheter system 10 may include one or more robotic catheter manipulator assemblies 300, for example, for manipulating catheter and sheath cartridges. Manipulator assembly 300 may include interconnected/interlocking manipulation bases for catheter and sheath cartridges. Each interlocking base may be capable of travel in the longitudinal direction of the catheter/sheath. In an embodiment, longitudinal travel may include a translation of up to 8 linear inches or more. Each interlocking base may be translated by a high precision drive mechanism. Such a drive mechanism may include, for example and without limitation, a motor driven lead screw or ball screw.

Robotic catheter manipulator assembly 300 may be usable with a robotic catheter rotatable device cartridge. Manipulator base may be replaced with a robotic catheter rotatable drive head and a robotic catheter rotatable drive mechanism.

As briefly discussed above, robotic catheter system 10 may include one or more cartridges 400, with manipulator 300 including at least two cartridges, each of which may be configured to control the distal movement of either the catheter or the sheath. With respect to a catheter cartridge, a catheter may be substantially connected or affixed to the cartridge, so that advancement of the cartridge correspondingly advances the catheter, and retraction of the cartridge retracts the catheter. Each cartridge may, for example, include slider blocks rigidly and independently coupled to one of a plurality of catheter steering wires in a manner to permit independent tensioning of each steering wire. The cartridge may be provided as a disposable item that is capable of being easily positioned (e.g., snapped) into place in an overall assembly. In an embodiment, the cartridge may include an electrical "handshake" device or component to allow the system 10 to properly identify the cartridge (e.g., by type and/or proper placement/positioning). A sheath cartridge may be designed in a similar manner as the catheter cartridge, but may be configured to provide for the passage of a catheter. The assembly may include a plurality (e.g., as many as ten or more) of independent driving mechanisms (e.g. motor driven ball screws).

Robotic catheter system 10 may be useful for a variety of procedures and in connection with a variety of tools and/or catheters. Such tools and/or catheters may include, without limitation, spiral catheters, ablation catheters, mapping catheters, balloon catheters, transseptal catheters, needle/dilator tools, cutting tools, cauterizing tools, and/or gripping tools. The system 10 may additionally include a means of identifying the nature and/or type of catheter/tool cartridge that is installed for use, and/or position or connection related information. It may also be desirable for the system 10 to automatically access/obtain additional information about the cartridge, such as, without limitation, its creation date, serial number, sterilization date, prior uses, etc.

Figure 2:
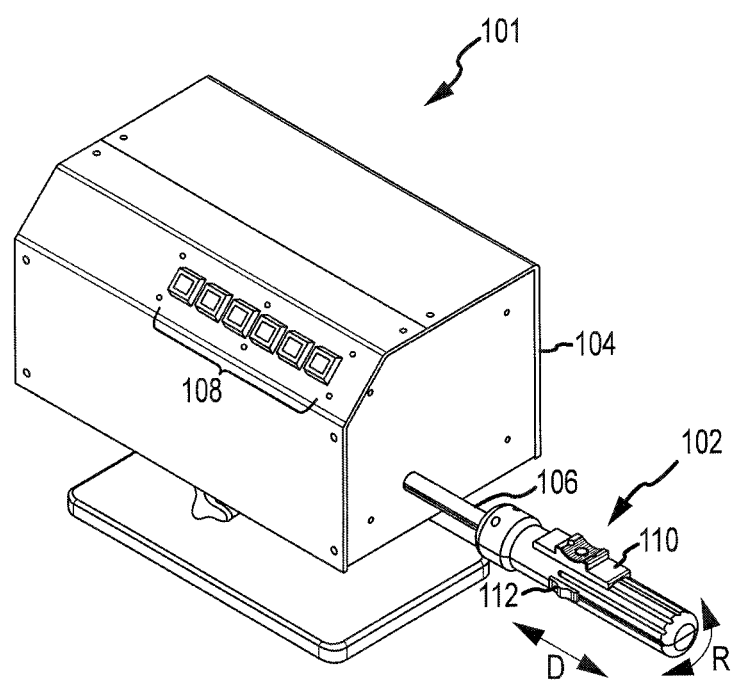
FIG. 2 is an isometric view of an input device according to an embodiment.

FIG. 2 illustrates an embodiment of an input device 101. Input device 101 may be configured to allow a user to selectively control a catheter, a sheath, or both a catheter and a sheath. Input device 101 may include at least one handle 102 connected to a control box 104 via a spline 106. As described in further detail below, control box 104 may be configured to receive inputs from a handle 102, such as user inputs from a user manipulating handle 102. Control box 104 may translate received user inputs into outputs, such as electrical signals, which may be used by a robotic catheter system 10 to control, e.g., a sheath and/or a catheter. Control box 104 may include one or more switches 108. Switches 108 may be configured to permit selection of one or more operating parameters, preset functions, or other functions such as: returning to a preset location, such as a home, or centered position; de-tensioning a catheter or sheath; reversing most recent movement; activating/deactivation ablation energy, etc. Handle 102 may be configured for motion relative to control box 104. In an embodiment, the motion of handle 102 relative to control box 104 may be similar to the motion of a traditional catheter handle. For instance, handle 102 may be configured to rotate in the direction R, and to be laterally displaceable, or translatable, in the direction of arrow D. Handle 102 may include one or more switches, such as switches 110, 112, as will be described further below with reference to FIG. 3. Control box 104 may be configured to detect motion of handle 102, and to generate one or more electrical or control signals in response thereto. The one or more control signals may be transmitted to robotic catheter system 10, such that manipulation of the handle 102 results in movement of a catheter and/or sheath in a manner similar to traditional catheter systems.

Figure 3A:
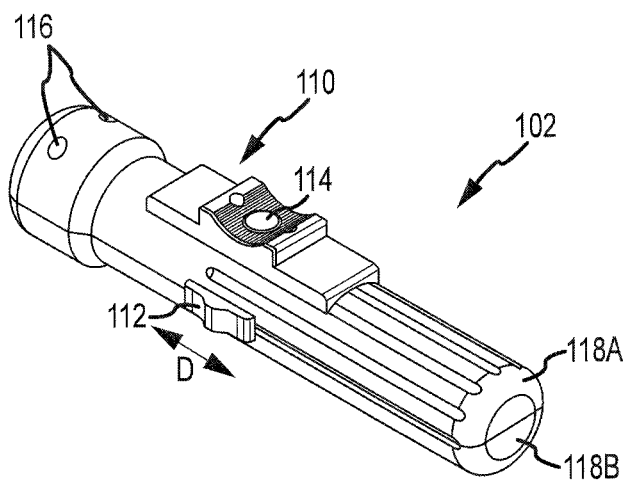
FIGS. 3A-3D are several views of a handle for an input device according to an embodiment.

FIG. 3A is an isometric view of a handle 102 according to an embodiment. Handle 102 includes a housing 118 comprising an upper portion 118A and a lower portion 118B. Handle 102 also includes a slider switch 110. Slider switch 110 may be configured to be selectively displaceable from a center position, generally in the direction of arrow D. In another embodiment, (not shown) slider switch 110 may be replaced with another switch, such as a deflection dial rotatable with respect to the handle, a thumb wheel, a toggle switch, or any other appropriate switch. In an embodiment, slider switch 110 may be configured to provide input representative of a desired deflection of the tip of a catheter and/or a sheath.

Handle 102 may also include a switch 112, which may, for example, comprise a three-position switch. Switch 112 may be configured to provide an input representative of a desired control scheme. For example, switch 112 may have a first position wherein manipulation of handle 102 results in corresponding manipulation of a catheter. Switch 112 may have a second position wherein manipulation of handle 102 results in a corresponding manipulation of a sheath. Switch 112 may also have a third position wherein manipulation of handle 102 results in a corresponding manipulation of both a catheter and a sheath. Selective control, or individual control, of each of a catheter and a sheath may be beneficial in that it may allow for compound movement and bending of the distal tip of the catheter and sheath. Combined control may be beneficial when it is desired that the catheter and the sheath move, for example, in a common direction, or along a common plane.

In the illustrated embodiment, upper portion 118A defines a plurality (in this case a pair) of apertures through which lights 116 may be visible. Lights 116 may be, for example, light emitting diodes (LEDs). A first light 116A may be configured to illuminate when switch 112 is positioned such that handle 102 controls a sheath. A second light 116B may be configured to illuminate when switch 112 is positioned such that handle 102 controls a catheter. In an embodiment, lights 116A, 116B may be configured to illuminate when switch 112 is positioned such that handle 102 controls both a sheath and a catheter. Lights 116A, 116B may be the same color, or may be different colors (e.g., colors associated with the components being controlled). As such, the use of different color lights may be useful in providing a user with contrasting indications of devices selected for control.

Handle 102 may include another switch, such as button 114, which may be embedded in slider switch 110. Button 114 may be configured to provide one or more inputs to control box 104 during operation. In an embodiment, button 114 may be configured to act as a device control switch, such as a dead-man switch. For example, in such an embodiment, if button 114 is not depressed, manipulation of handle 102 will not result in manipulation of an associated catheter or sheath. In another embodiment, button 114 may be configured to perform another function, such as providing an "on" signal for an associated ablation electrode. It is understood that handle 102 may also include one or more other switches (not pictured). A device control switch, or dead man switch, may also be implemented in another manner, such as by an optical relay or a capacitive switch which, when covered, indicates a user intends to manipulate an associated catheter or sheath.

Figure 3B:
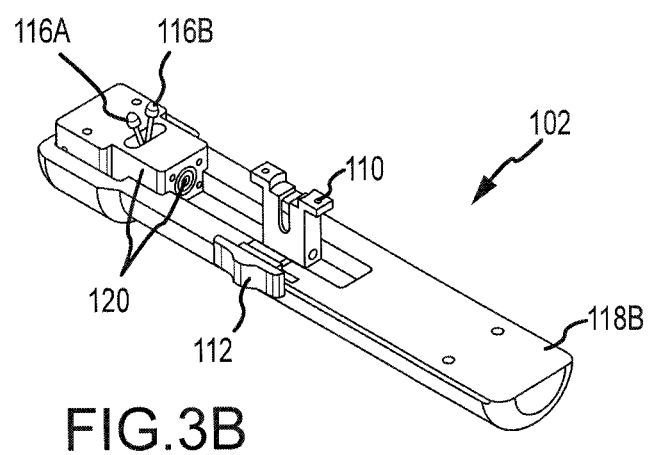

FIG. 3B is a partial exploded view of an embodiment of a handle 102 of the type generally illustrated in FIG. 3A. FIG. 3B illustrates embodiments of switches 110, 112, as well as lights 116A and 116B, mounted to lower portion 118B. Also illustrated is a bearing housing 120 which may be configured to assist in displacement of control rod 130 (as generally described in further detail with respect to FIG. 4C).

Figure 3C:
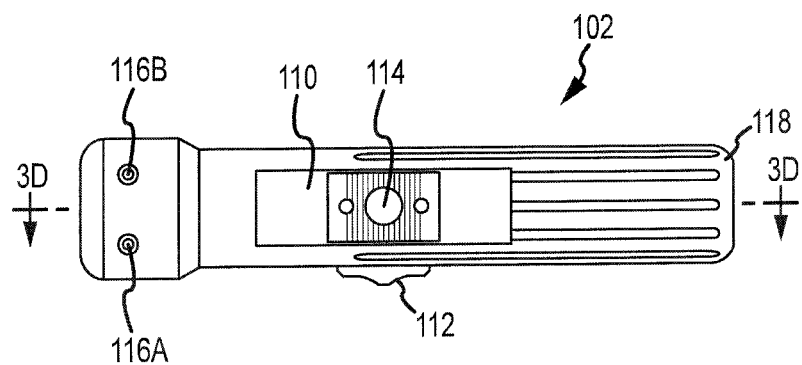
Figure 3D:
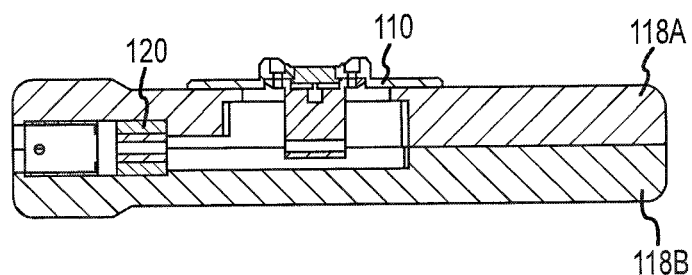

FIG. 3C is a top view of an embodiment of handle 102 as generally shown in FIG. 3A generally illustrating switches 110, 112, as well as lights 116A and 116B. FIG. 3D is a sectional view along line 3D-3D of FIG. 3C, further illustrating switch 110, as well as bearing housing 120. Bearing housing 120 may define an aperture through which a control rod may traverse (as generally described in further detail with respect to FIG. 4C).

Figure 4A:
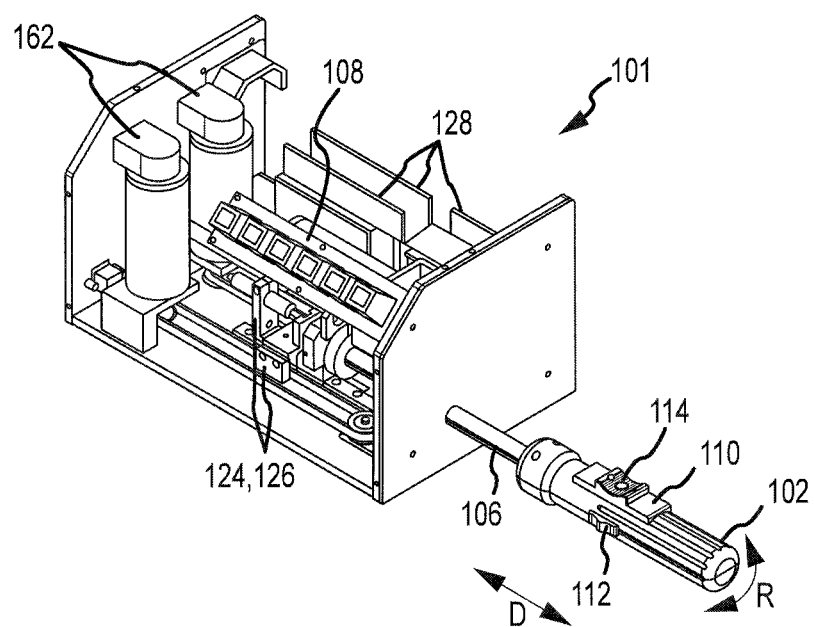
FIGS. 4A-4F are several views of a controller with an input device according to an embodiment.

FIG. 4A is an isometric view of input device 101 such as shown in FIG. 2 wherein the cover of control box 104 has been removed. FIG. 4A generally illustrates handle 102 coupled with control box 104 by spline 106. Other elements illustrated in FIG. 4A will be described in further detail below, with respect to FIGS. 4B and 4C.

Figure 4B:
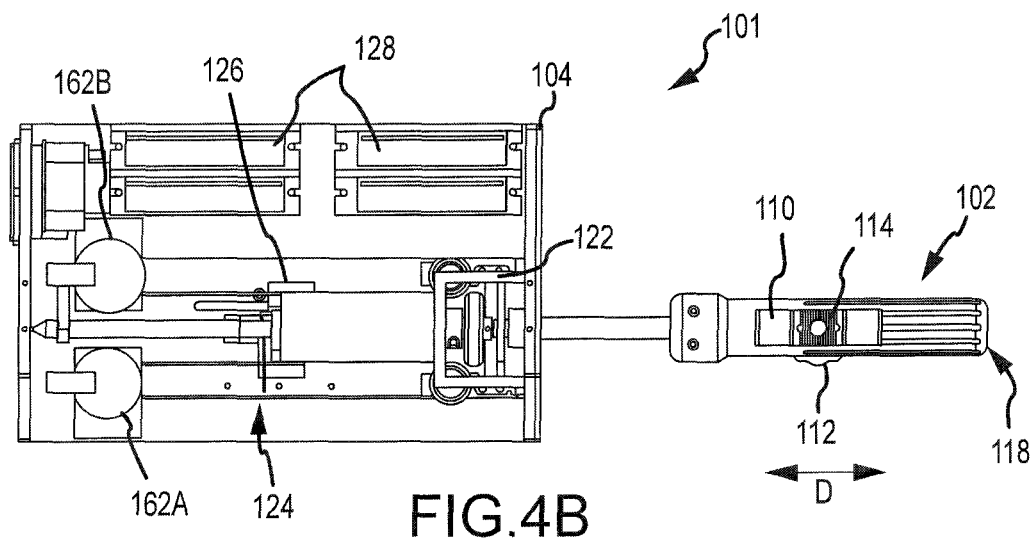

FIG. 4B illustrates a top view of input device 101 of FIG. 4A, wherein switches 108 have been removed. In the illustrated embodiment, input device 101 includes a handle, such as handle 102 illustrated in FIGS. 3A-3D, including switches 110, 112, and lights 116A, 116B coupled to housing 118. Handle 102 is coupled to housing 104 through spline 106. In an embodiment, spline 106 may be securely coupled to handle 102, such that manipulation of handle 102 induces a similar manipulation of spline 106. For example, when handle 102 is rotated relative to control box 104, spline 106 may rotate, transmitting the rotation to control box 104. Similarly, when handle 102 is translated with respect to control box 104 (i.e., laterally advanced or retracted, in the direction of arrow D), spline 106 may be similarly translated, thereby transmitting the translation to control box 104. In another embodiment (not illustrated), spline 106 could be rigid, and handle 102 could be configured to rotate and translate with respect to spline 106. In such an embodiment, handle 102 may include a rotary sensor and a translation sensor, wherein the rotary sensor could be configured to measure rotation of handle 102 with respect to spline 106, and the translation sensor could be configured to measure translation of handle 102 with respect to spline 106.

Control box 104 generally includes a number of mechanisms configured to receive inputs from handle 102 and to output those inputs as electrical signals, or outputs. Accordingly, control box 104 generally includes a rotation mechanism 122, a deflection mechanism 124, and a translation mechanism 126. Rotation mechanism 122 is configured to detect and/or measure rotational movement of handle 102. Deflection mechanism 124 is configured to detect and/or measure movement of slider switch 110. Translation mechanism 126 is configured to detect and/or measure translational movement of the handle 102. Control box 104 may also include an interface mechanism 128, which may be configured to transmit and/or receive one or more electrical signals, and/or to provide power to one or more of rotation mechanism 122, deflection mechanism 124, and translation mechanism 126. In another embodiment (not illustrated), slider switch 110 could be replaced with a deflection dial configured to rotate with respect to handle 102. A rotary potentiometer, or other rotary sensor, could detect rotation of the dial and transmit a signal representative of the rotation.

Figure 4C:
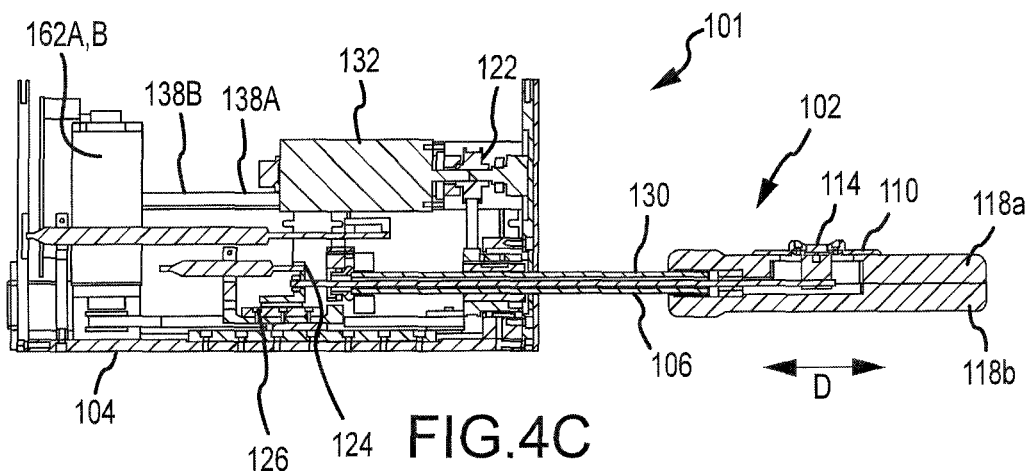

As illustrated in FIG. 4C, spline 106 may be hollow, defining an aperture therein. A switch control rod (or simply "control rod") 130 may be coupled to slider switch 110 to translate motion of slider switch 110 into control box 104. Control rod 130, which may be a hollow or a solid rod, may be configured to closely conform to an inner diameter of spline 106, and bearing housing 120, to allow control rod 130 to move within spline 106. Bearing housing 120 may include one or more linear bearings disposed therein to facilitate displacement of the control rod 130 within bearing housing 120.

Figure 4D:
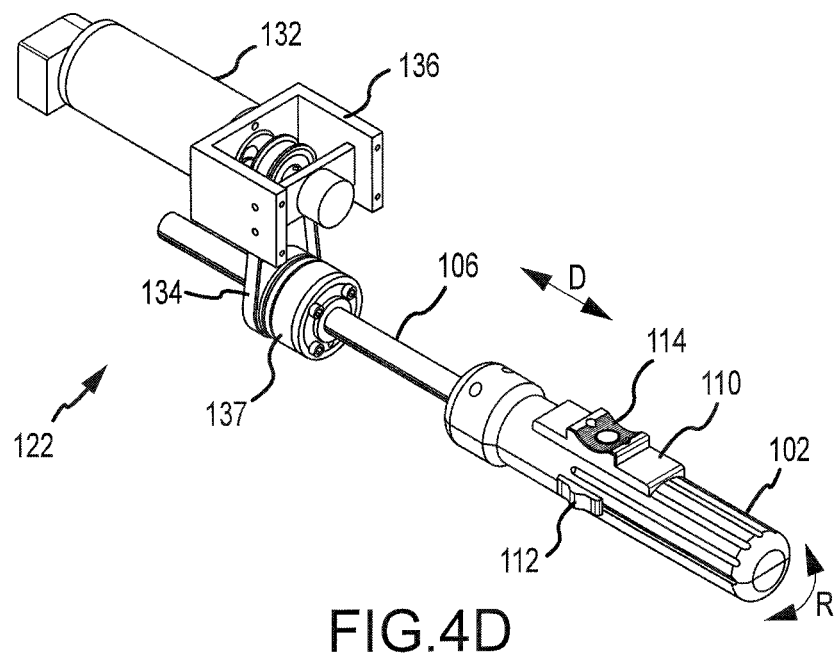

Rotational mechanism 122, as shown in FIG. 4D, may be configured to detect and/or measure rotational movement of handle 102, for example, in the direction denoted by arrow R. Rotational mechanism 122 generally includes a motor 132 and a rotational potentiometer 136 coupled to spline 106. Motor 132 may be coupled to rotational potentiometer 136. Rotational potentiometer 136 may be connected to a hub 137, which hub 137 is connected to the spline 106, using a belt 134.

Spline 106 may be configured such that rotation of spline 106 causes a corresponding rotation of rotational potentiometer 136, through the rotation of belt 134. In an embodiment, spline 106, hub 137 and rotational potentiometer 136 may be configured such that spline 106 may be displaced laterally (e.g., in the direction of arrow D) with respect to rotational potentiometer 136, independently of rotation of spline 106 and rotational potentiometer 136. That is, spline 106 may be translated in a direction generally corresponding to arrow D without any substantial effect on rotational potentiometer 136. In another embodiment (not pictured), rotational potentiometer 136 may be configured to be displaced laterally in a manner consistent with lateral displacement of spline 106.

Motor 132 may be configured to rotate in response to a rotation of spline 106. Rotation of motor 132 may be driven in a direct-drive manner, without any intermediate gearing or reduction of power or speed. That is, rotation of motor 132 may be directly resultant from a rotation of spline 106. Alternatively, rotation of motor 132 may be indirect, such as through belt 134, rotational potentiometer 136, and/or hub 137. When rotated, rotational potentiometer 136 may be configured to transmit a signal to, for example, a controller (not pictured) or an electronic interface, such as interface mechanism 128. The controller, or interface mechanism 128, may receive the signal from rotational potentiometer 136 and may determine one or more properties of the rotation. For example, the angle of rotation may be determined based on the number of counts received by a controller, or a voltage change of a potentiometer, and the speed of rotation could be determined by computing the time derivative of the calculated position.

In an embodiment, motor 132 may be configured to cause rotational movement of spline 106. For example, the system may include a self-centering feature, wherein spline 106, and handle 102, may return to a home position, as if connected to a torsional spring. Motor 132 may be configured to receive a signal from a controller, such as interface mechanism 128, which may cause motor 132 to return spline 106 to the home position.

Figure 4E:
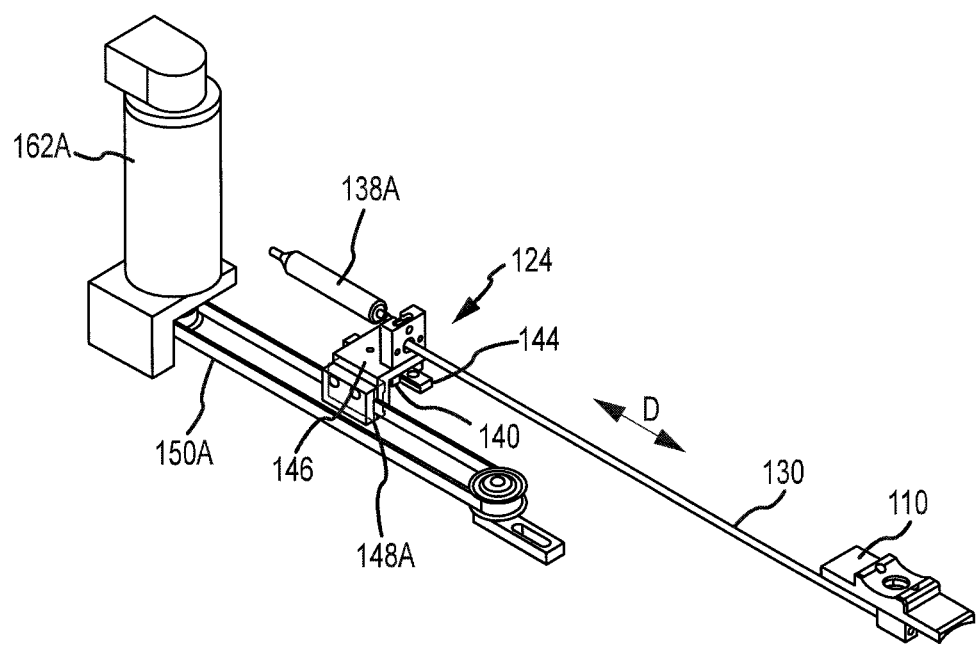

Deflection mechanism 124, as generally illustrated in FIG. 4E, may be configured to detect and/or measure linear displacement of a switch, such as slider switch 110, in a direction such as corresponding to arrow D. As mentioned previously, slider switch 110 may be coupled to control rod 130, which may translate lateral motion of slider switch 110 into control box 104 through an aperture defined within spline 106. In an embodiment, control rod 130 may be coupled at a distal end to a linear potentiometer 138A. Linear potentiometer 138A may be configured to detect and/or measure linear displacement of control rod 130, and thus may detect and/or measure linear displacement of slider switch 110. Linear potentiometer 138A may be electrically connected to a controller (not shown) and/or may be connected to an interface, such as interface mechanism 128. Linear potentiometer 138A may be configured to provide an output signal in response to linear motion of control rod 130, which may be used by a controller, such as interface mechanism 128. The received signal may be used to determine one or more of the speed, the direction, the force, and the magnitude of the displacement.

Figure 4F:
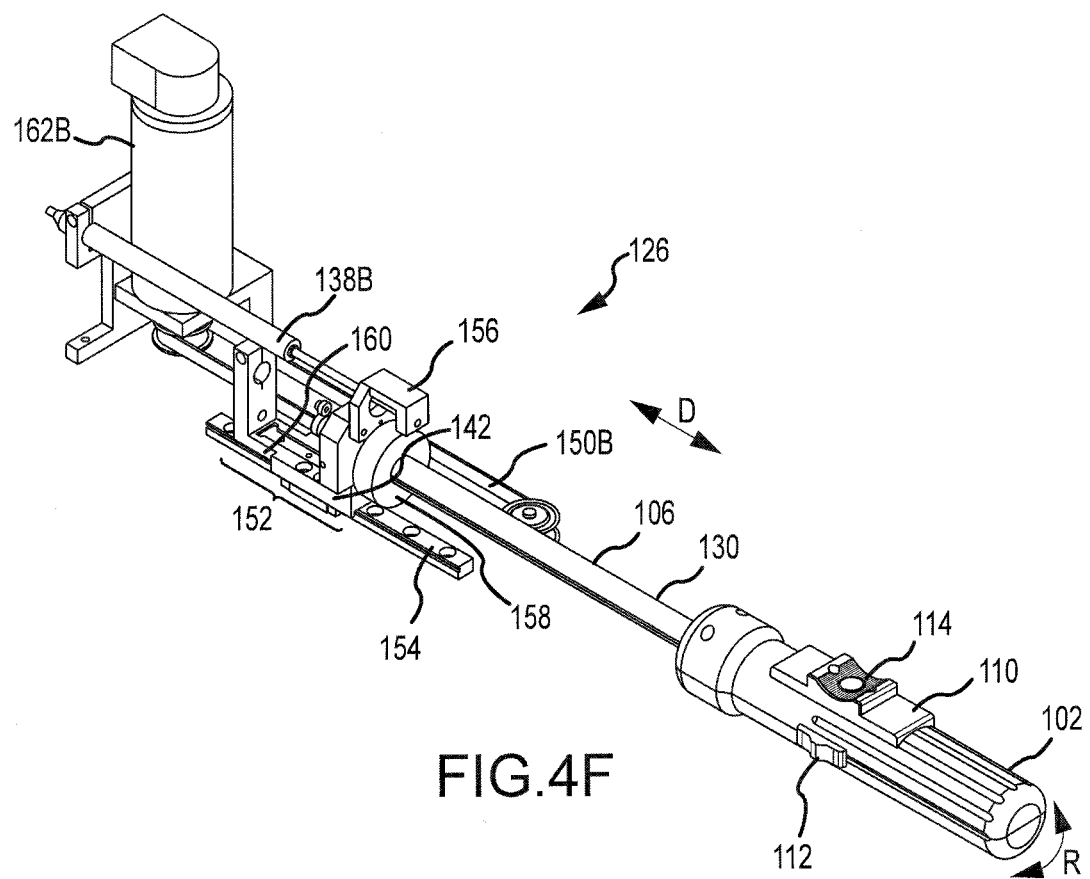

Translation mechanism 126, as generally illustrated in FIG. 4F, may be configured to detect and/or measure linear displacement of handle 102, in a direction such as corresponding to arrow D. In an embodiment, handle 102 may be coupled to a proximal end of spline 106. Spline 106 may be coupled at a distal end to a linear potentiometer 138B. Linear potentiometer 138B may be configured to detect and/or measure linear displacement of spline 106, and thus may detect and/or measure linear displacement of handle 102. Linear potentiometer 138B may be electrically connected to a controller (not shown) and/or may be connected to an interface, such as interface mechanism 128. Linear potentiometer 138B may be configured to provide an output signal in response to linear motion of handle 102, which may be received by the controller, such as interface mechanism 128. The received signal may be used to determine one or more of the speed, the direction, the force, and the magnitude of the linear displacement of handle 102.

Deflection mechanism 124 and translation mechanism 126 may be mounted to respective bases, 140, 142. In an embodiment, deflection base 140 may be configured to interact with translation base 142, for example, as further described below. As illustrated in FIG. 4E, an embodiment of a deflection base 140 may include a deflection rail 144 along which a deflection body 146 may translate laterally. Deflection body 146 may be coupled to control rod 130, and to a plunger of linear potentiometer 138A. Deflection body 146 may also be coupled to a belt clamp 148A, which is configured to be securely coupled to a belt 150A. When control rod 130 is displaced, deflection body 146 may also be displaced, which may cause plunger of linear potentiometer 138A to be pushed into the outer cylinder of linear potentiometer 138A. Distal displacement of control rod 130, and the corresponding displacement of displacement body 146 of deflection mechanism 124, may cause a rotation of belt 150A, as further described below.

In an embodiment, as illustrated in FIG. 4F, translation base 142 may include a translation body 152 configured to translate along a translation rail 154 in response to translation of handle 102. Translation rail 154 may be secured, for example, to a lower inner face of control box 104. Translation body 152 may include a proximal riser 156 configured to support spline 106. Riser 156 may support spline 106 directly or, for example, using a rotatable hub 158. Rotatable hub 158 may allow rotation of handle 102, and associated rotation of spline 106, to occur without imparting a significant torque on riser 156. Riser 156 may also be coupled to the plunger of linear potentiometer 138B. When handle 102 is translated, such as in a direction corresponding to arrow D, spline 106 may be similarly translated, which may impart a lateral force on hub 158. The force on hub 158 may cause riser 156 to move laterally, forcing the plunger of linear potentiometer 138B into the cylinder of linear potentiometer 138B. As riser 156 is translated, translation body 152 may move laterally along the rail 154. Translation body 152 may also include a belt clamp 148B (not pictured) coupled to a belt 150B. Movement of translation body 152 may cause belt 150B to move.

As illustrated, for example, in FIGS. 4A-4F, deflection mechanism 124 may be mounted on translation mechanism 126. In an embodiment, translation body 152 may include a groove 160 defined therein. Deflection rail 144 may be configured to be coupled in groove 160. In such an embodiment, linear potentiometer 138A may be coupled, at a distal end, to translation body 152. Deflection mechanism 124 may be configured such that linear displacement of translation mechanism 126, such as displacement along the direction of arrow D, will not affect deflection mechanism 124. That is, the entire deflection mechanism 124 may move laterally, resulting in no net change in the deflection mechanism 124. Accordingly, deflection may be maintained without impairing the ability to translate handle 102.

Each of the belts 150A, 150B may be configured to couple deflection mechanism 124 and translation mechanism 126 to respective motors 162A, 162B. In an embodiment, motors 162A, 162B may be coupled with an associated controller, and/or may be connected to interface mechanism 128. Motors 162A, 162B may transmit signals representative of motion induced on the motor, such as by induction mechanism 124 or translation mechanism 126. Additionally, or alternatively, motors 162A and 162B may be configured to induce motion of respective mechanisms 124, 126. For example, the system may be equipped with a self centering feature. Motor 162A may be configured to receive signals from an interface, such as interface mechanism 128, and to induce motion in deflection mechanism 124 to return deflection mechanism 124 to an initial or a centered state. "Centered state" may refer to the geometric center of the available motion of the deflection slider switch 110. "Centered state" may, additionally or alternatively, refer to a preset position or state programmable prior to, or during, a procedure. Similarly, motor 162B may be configured to receive position signals, and to return translation mechanism 126, and the associated spline 106, to a centered state.

Figure 5:
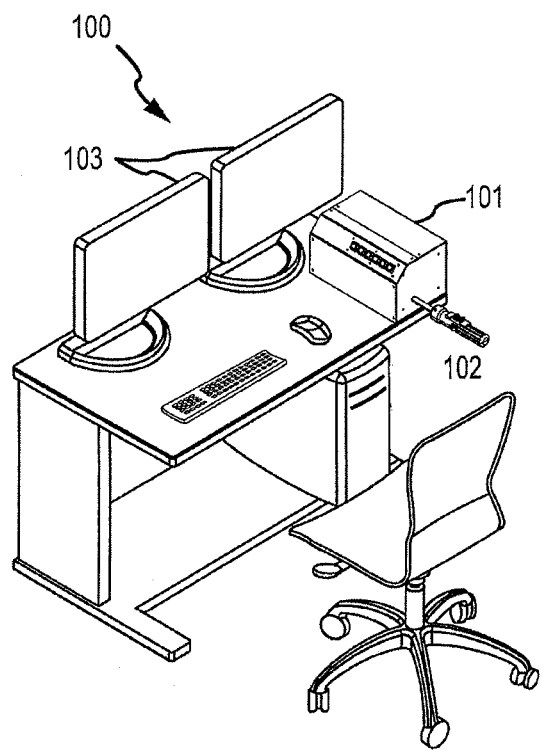
FIG. 5 generally illustrates an input system according to an embodiment.

FIG. 5 generally illustrates an exemplary input system 100. Input system 100 includes a computing system 102 configured to receive control signals from input device 101, and to display information related to the input control system 100 on one or more displays 103. Displays 103 may be configured to provide visual indications related to patient health, equipment status, catheter position, ablation related information, or other information related to catheter procedures. Computing system 102 may be configured to receive signals from input device 101, and to process those signals. For example, computing system 102 may receive signals indicative of a desired motion of a catheter within a patient, may format those signals, and transmit the signals to a manipulator system, such as manipulator system 300. The manipulator system may receive the signals and cause a corresponding motion of the catheter. Position, location, and movement of an associated catheter or sheath may be displayed to a user, such as an electrophysiologist, on display 103. The relationship between the movement of the input device 101 and an associated catheter and/or sheath may be affected in part by one or more control parameters or settings associated with computing system 102. Control parameters or settings may be provided by a user, such as an EP, through manipulation of software associated with computing device 102, through one or more inputs (e.g. inputs 108), or through other conventional control means. Control parameters or settings may include, without limitation, scaling values which may affect the magnitude or velocity at which the associated catheter or sheath is displaced in response to a given user input. For example, a scaling value of 2 may result in a catheter or sheath moving twice the distance that the catheter or sheath would move with respect to a scaling value of 1.

Figure 6A:
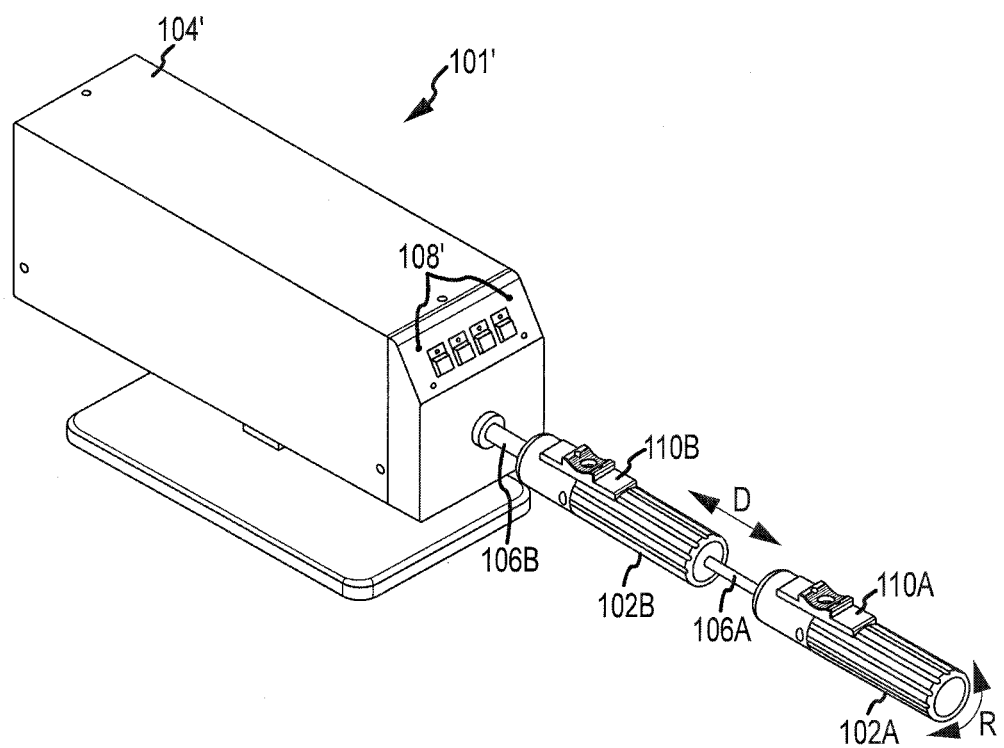
FIGS. 6A and 6B are isometric and side views, respectively, of an input device according to an embodiment.

FIG. 6A is an isometric view of an input device 101' according to a another embodiment. In the illustrated embodiment, input device 101' includes a first handle 102A and a second handle 102B. A first spline 106A is illustrated extending through a proximal end of handle 102B, and is coupled with handle 102A. A second spline 106B is coupled to a distal end of handle 102B, and with control box 104'. Each of handles 110A and 110B include a slider switch 112A, 112B.

In an embodiment, handle 102A may be configured to control a catheter, and handle 102B may be configured to control a sheath. In such an embodiment, handles 102A, 102B may be configured to move independently. Slider switch 110A may be configured to control deflection of an associated catheter, and slider switch 110B may be configured to control deflection of an associated sheath.

Figure 6B:
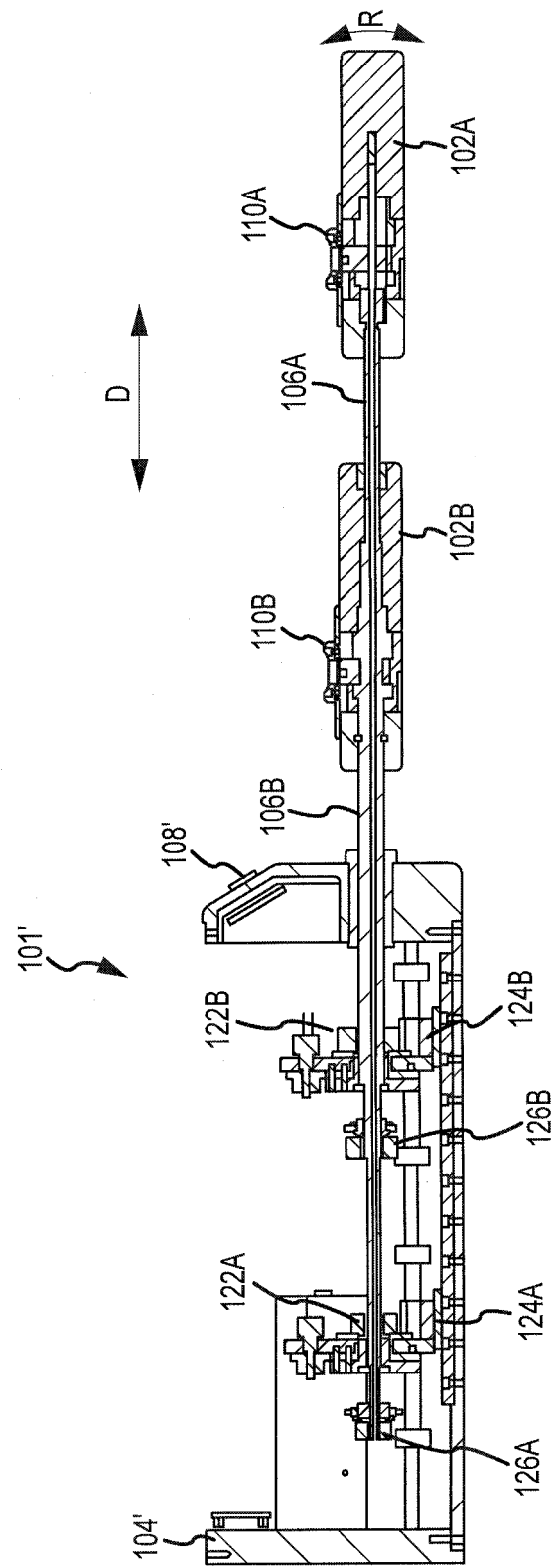

FIG. 6B is an isometric view of input device 101' as generally shown in FIG. 6A, further illustrating the mechanisms housed within control box 104'. Input device 101' generally includes a first rotation mechanism 122A, a first deflection mechanism 124a, and a first translation mechanism 126A, as well as a second rotation mechanism 122B, a second deflection mechanism 124B, and a second translation mechanism 126B. Operation of the mechanisms may be similar to the operation described in further detail above with respect to the foregoing drawings. Mechanisms 122A, 124a, and 126A are coupled with first handle 102A, and are respectively configured to detect rotation, deflection, and translation of handle 102A, as well as to transmit signals representative thereof to an associated controller. Mechanisms 122B, 124B, and 126B, as similarly coupled with second handle 102B, and are respectively configured to detect rotation, deflection, and translation of handle 102B, and to transmit signals representative thereof to an associated controller.

In an embodiment, handles, such as handle 102, 102A, 102B, may be configured to be removable and replaceable. For example, a first user may prefer a handle 102 having a slider switch 110 to control deflection. A second user may prefer a handle 102 having a dial switch (not pictured) to control deflection. A handle 102 may be configured to be easily removed and replaced with a handle including varying methods of providing input.

Figure 7A:
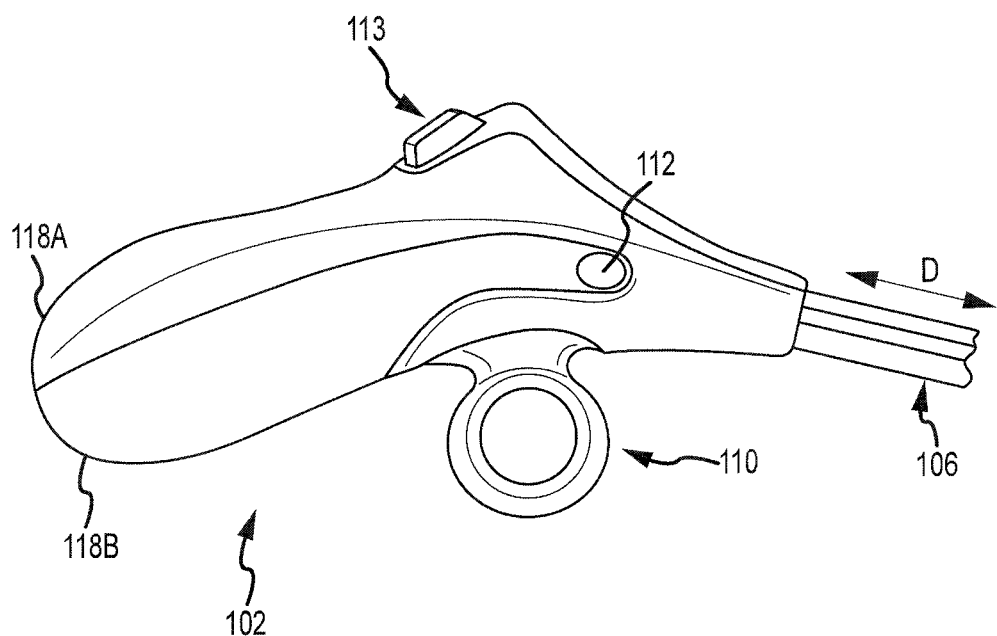
FIGS. 7A and 7B are side and isometric views, respectively, of an embodiment of a handle for an input device.
Figure 7B:
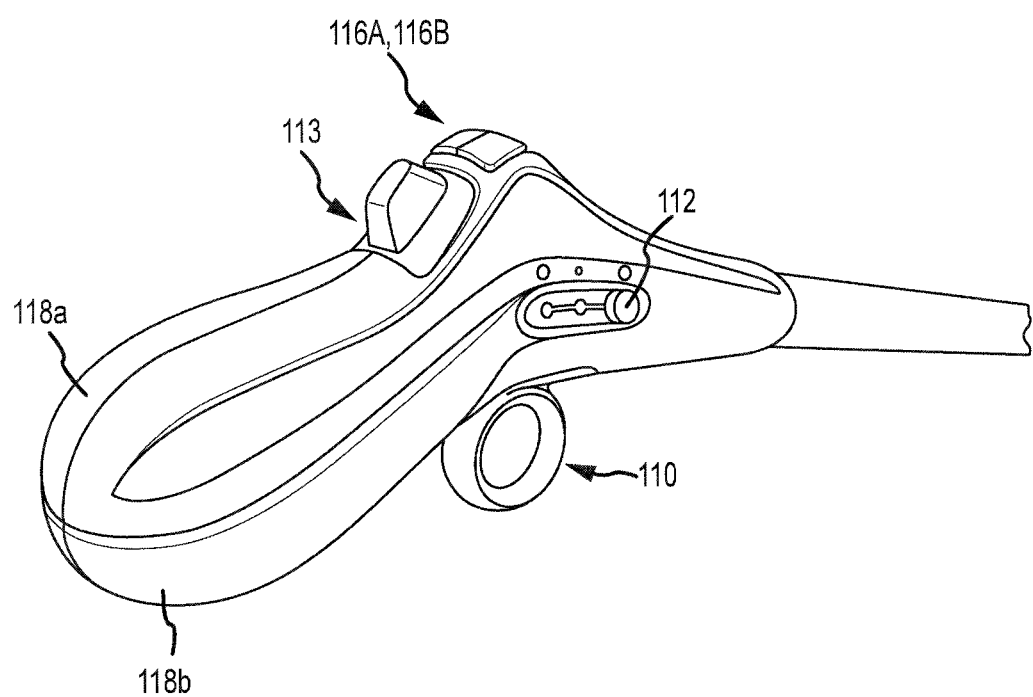

FIGS. 7A-7B illustrate an additional embodiment of a handle 102 for use with an input device 101. Handle 102 includes a trigger switch 110 which may, for example, be configured to control the distal end of a medical device, such as a catheter and/or a sheath. A switch 112 may be configured to allow a user to select one or both of a catheter and sheath for control. A rotation input 113 may be configured to allow a user to control rotation of an associated medical device, such as a catheter and/or sheath. In an embodiment, housing 118, which may include an upper housing 118A and lower housing 118B, and may be soft, contoured, or textured to allow for a more comfortable grip. Handle 102 may be configured to allow a user to control translation of a catheter and/or sheath, such as by pushing or pulling handle 102 along spline 106, generally in the direction of arrow D. Handle 102 may further include lights (not shown) to indicate the position of switch 112, which may provide an indication of one or more medical instruments selected for control.

Figure 7C:
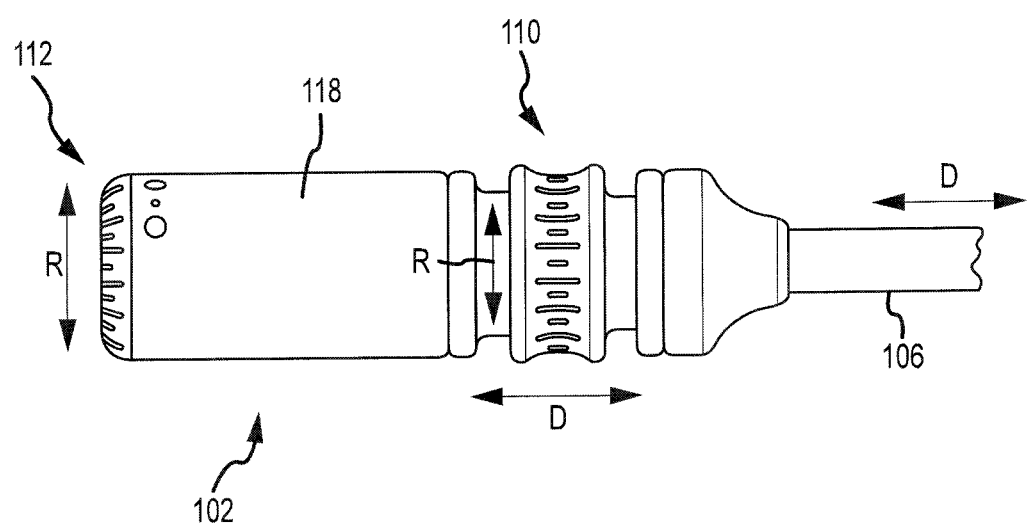
FIGS. 7C and 7D are side and isometric views, respectively, of another embodiment of a handle for an input device.
Figure 7D:
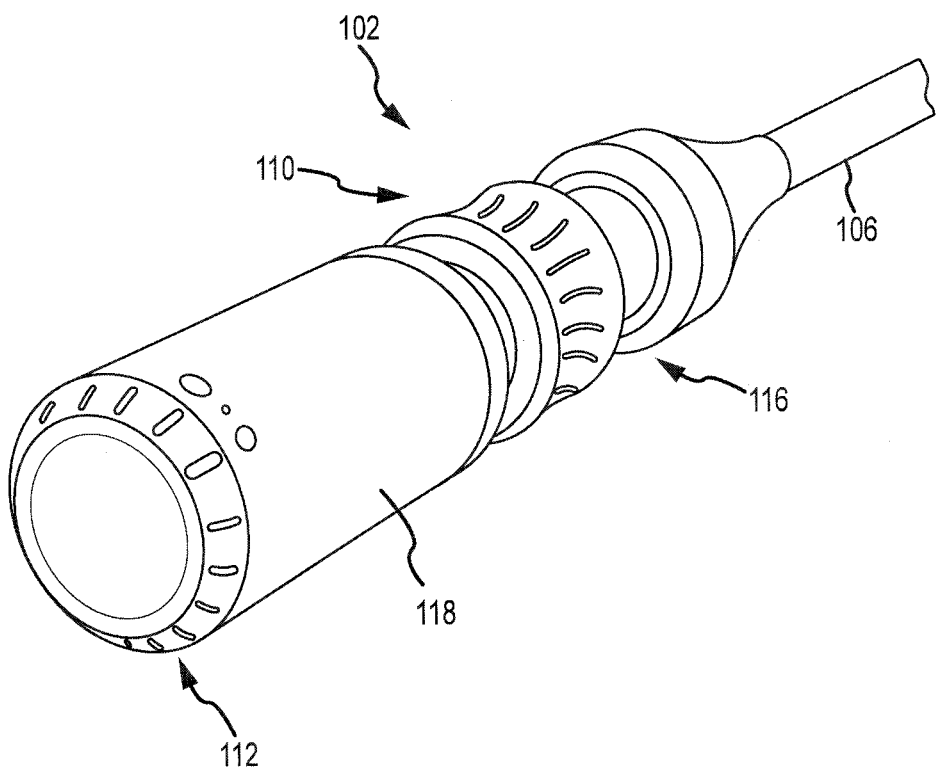

FIGS. 7C and 7D illustrate another embodiment of a handle 102 for use with an input device 101 (see, e.g., FIG. 2). Handle 102 includes a rotary switch 110 which may be displaceable in the direction of arrow D. Switch 110 may be configured such that displacement of switch 110 in the direction of the arrow D may control deflection of the distal end of an associated medical device, such as a catheter and/or a sheath. Switch 110 may be further configured such that rotation of switch 110 may control rotation of a catheter and/or sheath. Handle 102 may include a second switch 112, which may be a second rotary switch. Switch 112 may be configured to allow a user to select one or both of a catheter and sheath for control. Housing 118, which may include an upper housing 118A and a lower housing 118B, may be soft, contoured, and/or textured to allow for a more comfortable grip. Translation of a catheter and/or sheath may be controlled by pushing or pulling handle 102 along spline 106, generally in the direction of arrow D. Rings of lights 116 may be provided, and may be configured to indicate the position of switch 112, which may provide an indication of one or more associated medical instruments selected for control.

Figure 7E:
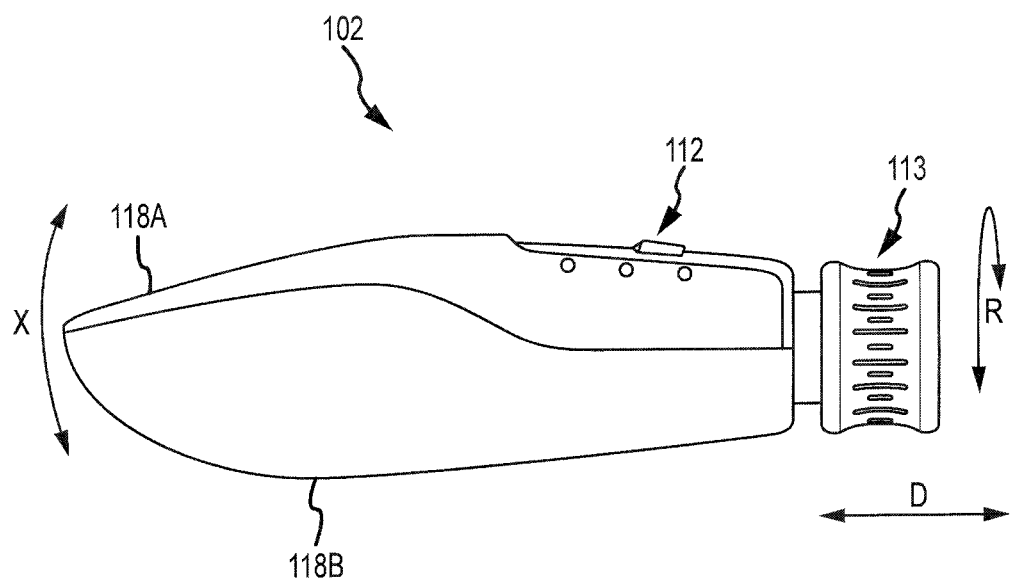
FIGS. 7E and 7F are side and isometric views, respectively, of yet another embodiment of a handle for an input device.
Figure 7F:
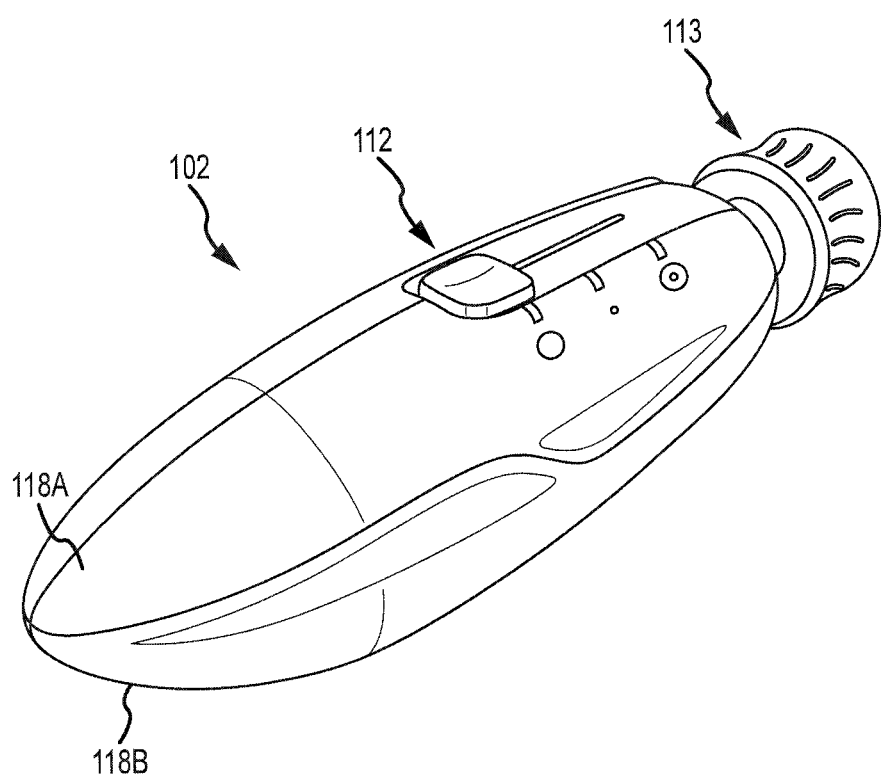

FIGS. 7E-7F generally illustrate another embodiment of a handle 102 for use with an input device 101. Handle 102 may be configured such that moving handle 102 up or down, generally in the direction of arrow X, may control deflection of the distal end of an associated medical device, such as a catheter and/or sheath. Handle 102 may include a switch 112 which may allow selection of one or more associated medical devices, such as selection of one or both of a catheter and sheath, for control. Handle 102 may include a rotation input 113 which may be configured to allow a user to control rotation of a catheter and/or sheath. Housing 118 may be soft, contoured, textured, etc., to provide a user with a more comfortable grip. Translation of a catheter and/or sheath may be controlled by pushing or pulling handle 102 along spline 106, generally in the direction of arrow D. Lights 116A, 116B may be used to indicate the position of switch 112, which may provide an indication of one or more medical instruments selected for control.

FIGS. 7G-7I illustrate yet another embodiment of a handle 102 for use with an input device 101. Handle 102 may be configured such that moving handle 102 up or down, generally in the direction of arrow X (FIG. 7G), may control translation of the distal end of an associated catheter and/or sheath. Handle 102 may be further configured such that moving handle 102 to one side or the other, generally in the direction of arrow Y (FIG. 7H), may control deflection of the distal end of an associated catheter and/or sheath. Handle 102 may be further configured such that rotating handle 102, for example, in the direction of arrow R (FIG. 7I), may control rotation of an associated catheter and/or sheath. Handle 102 may include a selector switch 112 which may allow selection of one or both of a catheter and sheath for control.

Figure 8A:
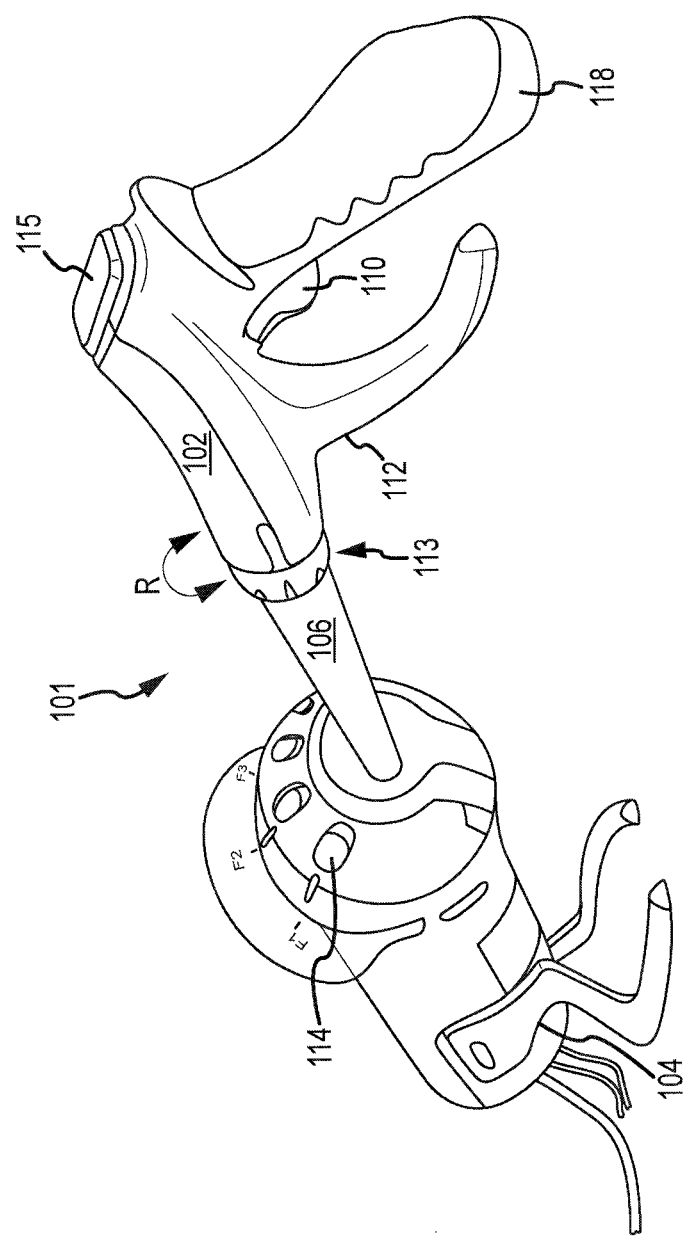
FIGS. 8A and 8B are isometric views of an input device according to an embodiment.

FIG. 8A generally illustrates an input device 101 including a handle 102 which may be coupled to a control box 104 via spline 106. Handle 102 may include a switch 110 which may be configured to control deflection of an associated medical device, such as an associated catheter and/or sheath. Handle 102 may also include a toggle switch 112 which may be configured to allow, e.g., selection of one or both of a catheter and sheath for control. Handle 102 may further include a rotary switch 113 which may be configured to allow a user to control rotation of an associated catheter and/or sheath, such as by rotating switch 113 in the direction of arrow R. Handle 102 may further include a translation switch 115 which may be configured to control translation of an associated catheter and/or sheath. Housing 118 of handle 102 may include a contoured or textured grip, such as a silicone grip, for improved comfort. Control box 104 may include a switch 114, which may be configured to serve as a dead man switch. Control box 104 may also include one or more displays and indicators. For example, an acrylic display may be used to display functions. One or more lights 116 may be provided and may be used to indicate the position of switch 112, which may provide an indication of one or more medical instruments selected for control.

Figure 8B:
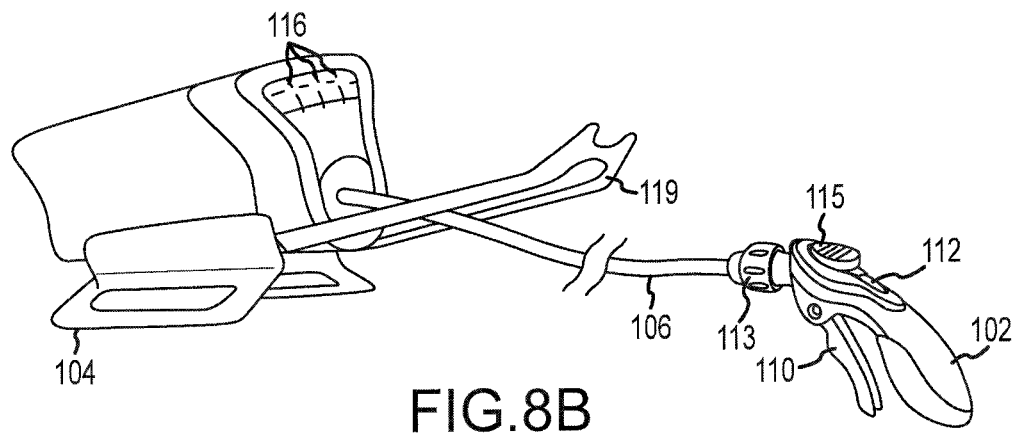
Figure 8C:
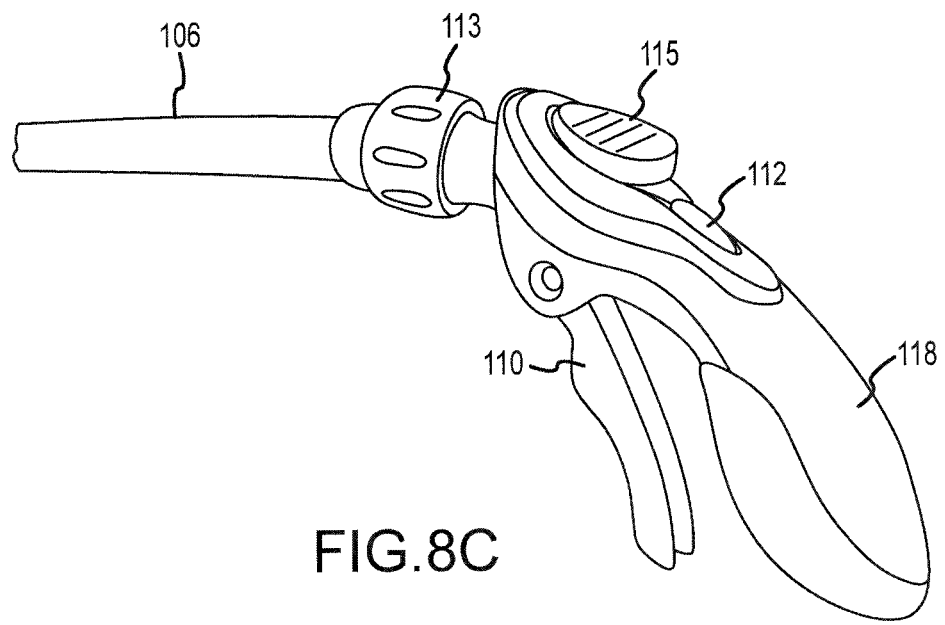
FIG. 8C is an isometric view of a handle of input device, the handle being of the type generally illustrated in FIGS. 8A and 8B.

FIG. 8B generally illustrates another embodiment of an input device 101, similar to the input device of FIG. 8A. FIG. 8C is an enlarged view of a handle 102 of the type shown in FIG. 8B. Handle 102 may be coupled to a control box 104 via spline 106. Spline 106 may be rigid, or may be flexible. Spline 106 may be configured to transmit one or more electrical signals between handle 102 and control box 104. Handle 102 may include a trigger switch 110 which may be configured to control deflection of an associated medical device, such as an associated catheter and/or sheath. The amount by which trigger switch 110 may travel may be adjustable. Handle 102 may also include a toggle switch 112 which may me configured to allow selection of one or both of a catheter and sheath for control. A rotary switch 113 may be configured to control rotation of an associated catheter and/or sheath, such as by rotating switch 113 in the direction of arrow R. Handle 102 may further include a translation switch 115 which may be configured to control translation of, e.g., an associated catheter and/or sheath. Housing 118 of handle 102 may include a textured grip, such as a silicone grip, for improved comfort. Control box 104 may also include one or more displays and indicators. For example, a display may be used to display functions. One or more lights 116 may be provided and may be configured to indicate the position of switch 112, and thereby provide an indication of one or more associated medical instruments selected for control. Control box may further include a holding rack 119, which may be retractable, may be configured, e.g., to hold handle 102 when handle 102 is not in use.

FIGS. 9A and 9B generally illustrate another embodiment of an input device 101 including a handle 102 coupled to a control box 104 via a spline 106. Handle 102 may include a generally spherical switch 110. Switch 110 may be configured such that rotation of switch 110 may allow a user to control rotation of an associated medical device, such as a catheter and/or sheath. Handle 102 may also include, or be coupled with, a second rotary switch 113 which may be configured such that rotation of switch 113 may control deflection of the distal end of an associated medical device, such as, a catheter and/or sheath. Handle 102 may include a toggle switch 112 which may be configured to allow a user to select, e.g., one or both of an associated catheter and sheath for control. Handle 102 may further include a switch 114 which may be configured to serve as a dead man switch 114.

Control box 104 may be coupled to a base 121 via one or more rotary couplers 123. Rotary couplers 123 may be selectively adjustable to allow changing of the angle of control box 104. Base 121 may include an emergency stop button 125, which may be configured to, e.g., retract an associated medical device, such as a catheter and/or sheath, or to remove ablation energy from an ablation catheter. Base 121 may further include one or more switches 127, which may be selectively assignable by a user.

FIGS. 10A, 10B and 10C generally illustrate an embodiment of a handle 102 for an input device. Handle 102 may be contoured, for example, to conform to the hand of a user. Handle 102 may be designed to conform to either a right hand or a left hand. Input may be provided to an input control system 100, for example, using a trackball 129 and one or more assignable buttons 131. Buttons 131 may be configured to allow a user to, e.g., select one or more of a catheter and sheath for control. Additionally, buttons 131 may be configured to allow a user to select a function which may be controlled using trackball 129. For instance, a first button 131A may be configured such that selection of button 131A causes trackball 129 to control deflection of the distal end of an associated catheter or sheath. A second button 131B may be configured such that selection of button 131B allows trackball 129 to control translation of an associated catheter or sheath. Moreover, handle 102 may be configured such that moving trackball 129 in a first direction, such as left or right, controls an associated catheter or sheath in a first manner, such as by controlling deflection of the catheter or sheath, and movement of trackball 129 in a second direction, such as forward and backward, controls an associated catheter or sheath in a second manner, such as by controlling translation. Handle 102 may include one or more mounting holes to allow handle 102 to be mounted, for example, on a machine, a table, or to another medical device.

Figure 11A:
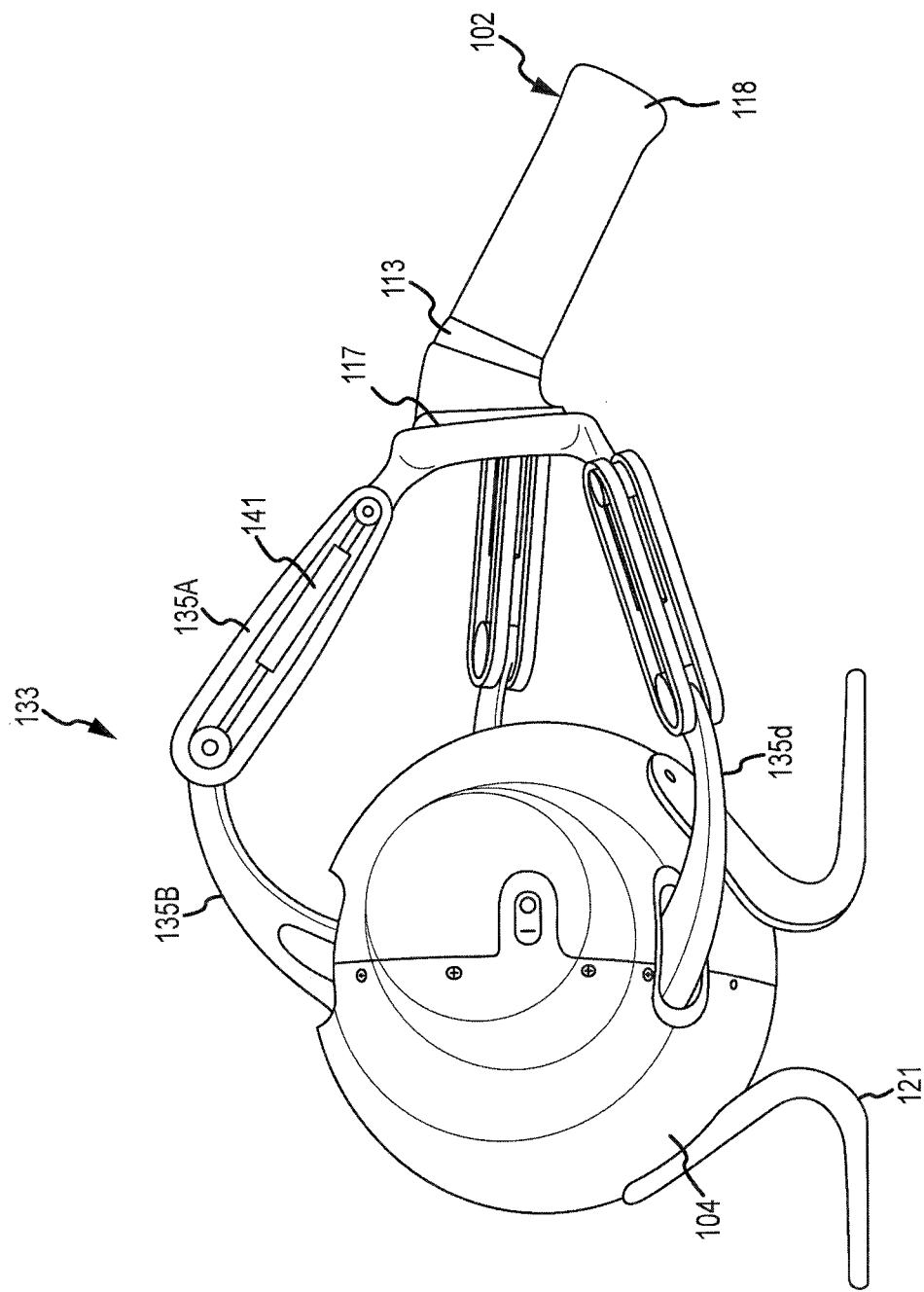
FIG. 11A is an isometric view of an input device according to an embodiment.
Figure 11B:
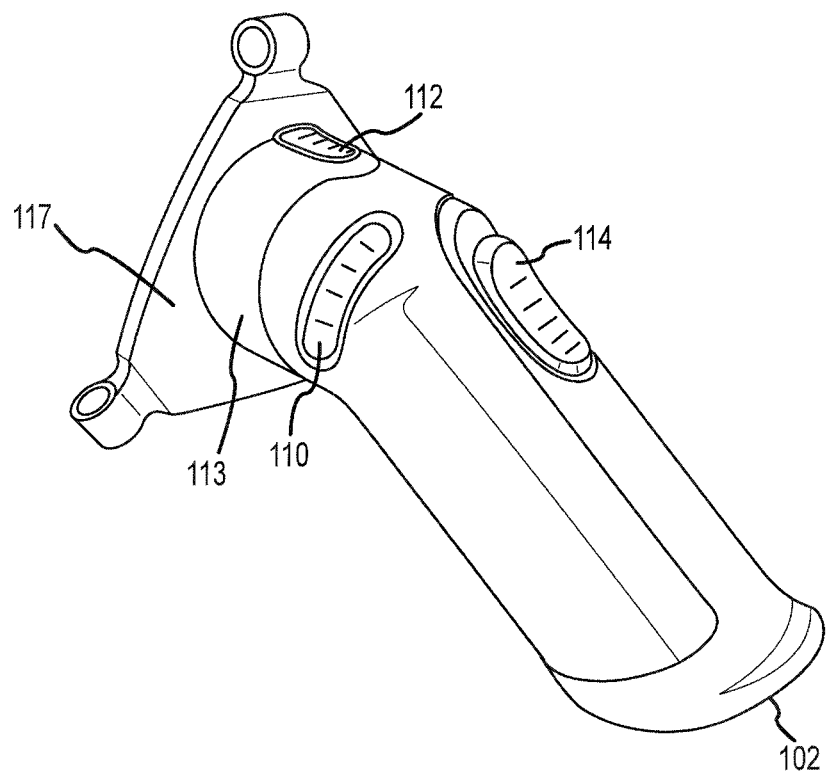
FIG. 11B is an isometric view of a handle, the handle being of the type generally illustrated in FIG. 11A.

FIG. 11A generally illustrates a side isometric of an input device 101 according to an embodiment. FIG. 11B generally illustrates an isometric view of a handle 102 which may be configured for use with input device 101. Input device 101 may be a spatial input device, which may be configured to allow a user to move handle 102 in three dimensions. Handle 102 may be coupled to a control box 104 via a plurality of control arms 133. Control arms 133 may include several sections 135A-135d which may pivot and collectively allow movement of handle 102 in a spherical plane. While FIG. 11A illustrates two control arms 133, it is to be understood that input device 101 may include any number of control arms 133. In an embodiment, input device 101 includes three control arms 133. One or more of sections 135 may be coupled to one or more motors, sensors, or controllers, such as motor 141. Handle 102 may be coupled to control arms 133 at a base 139, which may include one or more mounting points. Handle 102 may include a first rotary switch 110 which may be configured to allow a user to control an associated medical device, such as an associated catheter and/or sheath. For example, movement of handle 102 in the x-y plane may result in motion of the distal end of a catheter and/or sheath in the x-y plane. Movement of the handle 102 in the z-plane may result in translation, or advancement, of the distal end of an associated catheter and/or sheath. Additionally, or alternatively, rotation of switch 110 may control deflection of the distal end of an associated catheter and/or sheath. A toggle switch 112 may permit selection of one or both of a catheter and sheath for control. Handle 102 may include a housing 118 coupled to the one or more control arms 133 through a base 117. In one embodiment, housing 118 may be rigidly coupled to base 117. In a further embodiment, housing 118 may be rotatably coupled to base 117 through a rotary switch 113. Rotary switch 113 may be configured to allow a user to control one or more properties of an associated medical device. For example, rotary switch 113 may be configured to allow a user to rotate the distal end of an associated catheter and/or sheath. Handle 102 may further be configured such that the angle at which housing 118 couples to base 117 may be adjustable. Handle 102 may further include a switch 114 which may be configured to serve as a dead man switch 114.

Input device 101 may be configured such that control arms 133, and associated elements, may be configured to provide force feedback to a user. For example, motors, sensors, and/or controllers may be coupled to one or more of sections 135 of arms 133 to induce, assist or resist motion in a particular direction. Multiple motors, sensors, controllers, etc., may work in concert to induce, assist, or resist motion in a spherical manner. Moreover, input device 101 may be configured such that one or more of control arms 133, and/or one or more of sections 135, may be selectively lockable. For example, motor 141 may selectively power, or lock one or more of motors 141 to restrict handle motion 102. In an embodiment, input device 101 may restrict handle 102 motion to a particular plane, such as an x-y plane, or may, for example, prevent motion within the x-y plane while allowing handle 102 to translate and rotate on an axis, such as the Z-axis. In another embodiment, input device 101 may be configured to lock rotation along an axis, such as the Z-axis, while allowing handle 102 otherwise unrestricted movement.

Although embodiments of this invention have been described above with a certain degree of particularity, those skilled in the art could make numerous alterations to the disclosed embodiments without departing from the spirit or scope of this invention. For example, while embodiments have been described using potentiometers, it is to be understood that additional embodiment could include other types of sensors and encoders including, without limitation, absolute position encoders, relative position encoders, optical encoders, linear encoders, linear actuators, and linear variable differential transformers. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An input device for a robotic medical system including a medical instrument with a distal end, the input device comprising:
 an input device handle configured to remotely control said medical instrument, to be rotatable about an axis, and to be longitudinally displaceable along the axis;
 a first sensor configured to detect axial rotation of the input device handle;
 a second sensor configured to detect longitudinal displacement of the input device handle along the axis; and
 a deflection control element disposed on or about the input device handle and configured to selectively control deflection of said distal end of said medical instrument within a deflection plane via a control rod operatively connected to the deflection control element;
 a hollow spline operatively coupled with the input device handle, the hollow spline having an aperture configured to permit motion of the control rod within the aperture;
 wherein longitudinal displacement of the input device handle results in a corresponding longitudinal motion of said medical instrument, wherein the corresponding longitudinal motion of said medical instrument is proportional to the longitudinal displacement of the input device handle; rotation of the input device handle results in a corresponding rotation of the deflection plane, wherein the corresponding rotation of the deflection plane is proportional to the rotation of the input device handle; and the longitudinal displacement and rotation of the input device handle are detected electronically and outputted as electrical signals representative of the longitudinal displacement of the input device handle and the rotation of the input device handle.

2. The input device of claim 1, wherein said medical instrument includes at least one of a catheter and a sheath, and the input device includes a selection switch configured to permit selective control of the catheter, sheath, or catheter and sheath.

3. The input device of claim 2, further comprising one or more indicators indicating whether the input device handle is configured to remotely control the catheter, the sheath, or both the catheter and sheath.

4. The input device of claim 1, wherein the input device is configured to return to an initial or centered position after displacement.

5. The input device of claim 1, further comprising at least one sensor operatively connected or coupled to the input device handle, the at least one sensor configured to detect at least one of displacement of the input device handle, rotation of the input device handle, and displacement of a switch.

6. The input device of claim 5, further comprising a control system configured to receive from at least one of the first sensor and the second sensor the electrical signals representative of the longitudinal displacement of the input device handle and the rotation of the input device handle, format the electrical signals, and output the formatted electrical signals to a manipulator assembly configured to cause or result in a corresponding displacement of said medical instrument.

7. The input device of claim 6, wherein the velocity of the displacement of said medical instrument is proportional to the magnitude of the displacement of the at least one sensor.

8. The input device of claim 5, wherein the at least one sensor is at least one of a potentiometer, a motor, and an encoder.

9. The input device of claim 5, further comprising at least one servo motor configured to return the input device handle to an initial or centered position after displacement.

10. The input device of claim 9, wherein the at least one servo motor is coupled to the input device handle in a direct-drive configuration.

11. The input device of claim 1, further comprising a dead man switch that is configured to prevent unintentional control of said medical instrument.

12. The input device of claim 11, wherein the dead man switch is an optical switch or a capacitive switch configured to detect the presence or absence of a portion of a hand in contact with at least a portion of the input device handle.

13. The input device of claim 1, wherein the input device handle comprises a first input device handle and wherein the deflection control element disposed on or about the input device handle comprises a first deflection control element of a first type and wherein the first input device handle and the first deflection control element may be selectively removed and replaced with a second input device handle having a second deflection control element of a second type.

14. The input device of claim 1, further configured to provide haptic feedback to a user.

15. The input device of claim 14, wherein the input device is configured to provide at least one of heat, cold, a vibration or a force to a user through the input device handle.

16. The input device of claim 14, wherein haptic feedback is indicative of contact of the distal of a catheter or sheath with tissue within a treatment area.

17. The input device of claim 14, wherein haptic feedback is indicative of a physical property of the input device or an associated catheter or sheath.

18. A device for controlling the robotic movement of a catheter, the device comprising:
 a joystick input device including a first sensor configured to detect motion of the joystick input device in a first manner and a second sensor configured to detect motion of the joystick input device in a second manner; and
 a control system configured to receive a control signal from the first and second sensors and to transmit a corresponding motion-related command to a catheter manipulation mechanism, the control system coupled to the joystick input device via a plurality of control arms, the control arms configured to pivot and allow movement of the joystick input device in a spherical plane;
 wherein the control system is configured to relate displacement of the joystick input device in the first manner to a corresponding advancement or retraction of at least one of a catheter and a sheath, wherein the corresponding advancement or retraction of at least one of the catheter and the sheath is proportional to the displacement of the joystick input device in the first manner, and wherein the control system is configured to relate displacement of the joystick input device in the second manner to a corresponding deflection of the distal end of at least one of a catheter and a sheath along a deflection plane, wherein the corresponding deflection of the distal end of at least one of the catheter and the sheath along a deflection plane is proportional to the displacement of the joystick input device in the second manner.

19. The device of claim 18, further comprising at least one rotary input device, wherein activation of the rotary input device results in a corresponding rotation of the deflection plane.

20. The device of claim 19, wherein rotation of the rotary input device results in a corresponding rotation of a distal end of at least one of a catheter and a sheath.

21. The device of claim 19, wherein the rotary input device is at least one of a potentiometer, a motor, and an encoder.

22. The device of claim 18, wherein the first sensor and the second sensors each include at least one of a potentiometer, a motor, and an encoder.

23. The device of claim 18, further comprising at least one centering mechanism configured to return the joystick input device to an initial or neutral position after displacement.

24. The device of claim 23, wherein the centering mechanism includes at least one motor.

* * * * *